United States Patent [19]
Podsakoff et al.

[11] Patent Number: 5,846,528
[45] Date of Patent: Dec. 8, 1998

[54] TREATING ANEMIA USING RECOMBINANT ADENO-ASSOCIATED VIRUS VIRIONS COMPRISING AN EPO DNA SEQUENCE

[75] Inventors: Gregory M. Podsakoff, Fullerton; Gary J. Kurtzman, Menlo Park, both of Calif.

[73] Assignees: Avigen, Inc., Alameda, Calif.; Johns Hopkins University, Baltimore, Md.

[21] Appl. No.: 785,750

[22] Filed: Jan. 16, 1997

Related U.S. Application Data

[63] Continuation-in-part of Ser. No. 588,355, Jan. 18, 1996.

[51] Int. Cl.$^6$ .......................... A61K 48/00; C12N 5/00; C12N 15/00
[52] U.S. Cl. .................. 424/93.2; 424/93.21; 514/44; 514/814; 514/815; 435/320.1; 935/62
[58] Field of Search .................. 514/44, 814, 815; 424/93.2, 93.21; 435/320.1; 935/62

[56] References Cited

U.S. PATENT DOCUMENTS 5,252,479 10/1993 Srivastava .
5,589,362 12/1996 Bujard et al. .

FOREIGN PATENT DOCUMENTS

WO 94/13788  6/1994  WIPO .
WO 95/13376  5/1995  WIPO .
WO 95/20671  8/1995  WIPO .
WO 96/40272  12/1996  WIPO .

OTHER PUBLICATIONS

Kessler et al., "Gene Delivery to Skeletal Muscle Results in Sustained Expression and Systemic Delivery of a Therapeutic Protein," Proc. Natl. Acad. Sci. USA 93:14082–14087(1996).
Naffakh et al., "Long–Term Secretion of Therapeutic Proteins from Genetically Modified Skeletal Muscles," Human Gene Therapy 7:11–21 (1996).
Podsakoff et al., "AAV Vector–Mediated Gene Delivery to Skeletal Muscle In Vivo Results in Sustained Levels of Systemic Erythropoietin," Blood 88(10):1066 (1996).
Acsadi et al., "Human dystrophin expression in mdx mice after intramuscular injection of DNA constructs," Nature (1991) 352:815–818.
Acsadi et al., "Cultured human myoblasts and myotubes show markedly different transducibility by replication–defective adenovirus recombinants," Gene Therapy (1994) 1:338–340.
Acsadi et al., "A differential efficiency of adenovirus–mediated in vivo gene transfer into skeletal muscle cells of different maturity," Hum. Mol. Genetics (1994) 3:579–584.
Barr and Leiden, "Systemic delivery of recombinant proteins by genetically modified myoblasts," Science (1991) 254:1507–1509.
Bartlett et al., Am. J. Human Genetics (1995) 57 (Supp 4) #A235.
Blau and Springer, "Molecular medicine muscle–mediated gene therapy," New Eng. J. Med. (1995) 333:1204–1207.

Blau and Springer, "Molecular medicine gene therapy–a novel form of drug delivery," New Eng. J. Med. (1995) 333:1554–1556.
Dai et al., "Gene therapy via primary myoblasts: long–term expression of factor IX protein following transplantation in vitro," Proc. Natl. Acad. Sci. USA (1992). 89:10892–10895.
Dai et al., "Cellular and humoral immune responses to adenoviral vectors containing factor IX gene: tolerization of factor IX and vector antigens allows for long–term expression," Proc. Natl. Acad. Sci. USA (1995) 92:1401–1405.
Davis et al., "Direct gene transfer into skeletal muscle in vivo: Factors affecting efficiency of transfer and stability of expression," Hum. Gene Therapy (1993) 4:151–159.
Descamps et al., "Organoids direct systemic expression of erythropoietin in mice," Gene Therapy (1995) 2:411–417.
Dhawan et al., "Systemic delivery of human growth hormone by injection of genetically engineered myoblasts," Science (1991) 254:1509–1512.
Einerhand et al., "Regulated high–level human β–globin gene expression in erythroid cells following recombinant adeno–associated virus–mediated gene transfer," Gene Therapy (1995) 2:336–343.
Flotte et al., "Gene expression from Adeno–associated virus vectors in airway epithelial cells," Am. J. Respir. Cell Mol. Biol. (1992)7:349–356.
Flotte et al., "Expression of the cystic fibrosis transmembrane conductance regulator from a novel adeno–associated virus promoter," J. Biol. Chem. (1993) 268:3781–3790.
Flotte et al., "Stable in vivo expression of the cystic fibrosis transmembrane conductance regulator with an adeno–associated virus vector," Proc. Natl. Acad. Sci. USA (1993)90:10613–10617).
Flotte et al., "Adeno–associated virus vector gene expression occurs in nondividing cells in the absence of vector DNA integration," Am. J. Respir. Cell Mol. Biol. (1994) 11:517–521.
Gilgenkrantz et al., "Transient expression of genes transferred in vivo into heart using first–generation adenoviral vectors: role of the immune response," Hum. Gene Therapy (1995) 6:1265–1274.
Hamamori et al., "Persistent erythropoiesis by myoblast transfer of erythropoietin cDNA," Hum. Gene Therapy (1994) 5:1349–1356.

(List continued on next page.)

Primary Examiner—Deborah Crouch
Attorney, Agent, or Firm—Robins & Associates

[57] ABSTRACT

The use of recombinant adeno-associated virus (AAV) virions for delivery of DNA molecules to muscle cells and tissue in the treatment of anemia is disclosed. The invention allows for the direct, in vivo injection of recombinant AAV virions into muscle tissue, e.g., by intramuscular injection, as well as for the in vitro transduction of muscle cells which can subsequently be introduced into a subject for treatment. The invention provides for sustained, high-level expression of a delivered nucleotide sequence encoding erythropoietin, and for in vivo secretion thereof from transduced muscle cells such that systemic delivery is achieved.

34 Claims, 8 Drawing Sheets

OTHER PUBLICATIONS

Hamamori et al., "Myoblast transfer of human erythropoietin gene in a mouse model of renal failure," *J. Clin. Invest.* (1995) 95:1808–1813.

Kaplitt et al., "Long-term gene expression and phenotypic correction using adeno–associated virus vectors in the mammalian brain," *Nature Genetics* (1994) 8:148–154.

Knowles et al., "A controlled study of adenoviral–vector–mediated gene transfer in the nasal epithelium of patients with cystic fibrosis," *The New Eng. J. of Med.* (1995) 333(13):823–831.

Leiden, "Gene therapy–promise, pitfalls and prognosis," *New Eng. J. Med.* (1995) 333:871–872.

March et al., *Clin. Res.* (1992) 40(2):358A.

Mendell et al., "Myoblast transfer in the treatment of Duchenne's muscular dystrophy," *New Eng. J. Med.* (1995) 333:832–838.

Naffakh et al., "Sustained delivery of erythropoietin in mice by genetically modified skin fibroblasts," *Proc. Natl. Acad. Sci.* (1995)92:3194–3198.

Osborne et al., "Gene therapy for long–term expression of erythropoietin in rats," *Proc. Natl. Acad. Sci.* (1995)92:8055–8058.

Podsakoff et al., "Efficient gene transfer into nondividing cells by adeno–associated virus–based vectors," *J. Virol.* (1994) 68:5656–5666.

Quantin et al., "Adenovirus as an expression vector in muscle cells in vivo," *Proc. Natl. Acad. Sci. USA* (1992) 89:2581–2584.

Raz et al., "Systemic immunological effects of cytokine genes injected into skeletal muscle," *Proc. Natl. Acad. Sci. USA* (1993) 90:4523–4527.

Russell et al., "Adeno–associated virus vectors preferentially transduce cells in S phase," *Proc. Natl. Acad. Sci. USA* (1994) 91:8915–8919.

Villeval et al., "Retrovirus–medicated transfer of the erythropoietin gene in hematopoietic cells improves the erythrocyte phenotype in murine $\beta$–thalassemia," *Blood* (1994) 84(3):928–933.

Wolff et al., "Direct gene transfer into mouse muscle in vivo," *Science* (1990) 247:1465–1468.

Wolff et al., "Long–term persistence of plasmid DNA and foreign gene expression in mouse muscle," *Human Mol. Genet.* (1992) 1:363–369.

Xiao et al., "Adeno–associated virus (AAV) vectors for gene transfer," *Advanced Drug Delivery Reviews* (1993) 12:201–215.

Xiao et al., "Efficient long–term gene transfer into Muscle tissue of immunocompetent mice by adeno–associated virus vector," *J. of Virol.* (1996) 70(11):8098–8108.

```
                   10         20         30         40         50         60
         tggtcacccg gcgcgcccca ggtcgctgag ggaccccggc caggcgcgga gATGGGGGTG      60
  1   CACGAATGTC CTGCCTGGCT GTGCTTCTC CTGTCCCTGC TGTCGCTCCC TCTGGGCCTC     120
 61   CCAGTCCTGG GCGCCCCACC ACGCCTCATC TGTGACAGCC GAGTCCTGGA GAGGTACCTC     180
121   TTGGAGGCCA AGGAGGCCGA GAATATCACG CTGAACACTG CAGCTTGAAT                240
181   GAGAATATCA CTGTCCCAGA CACCAAAGTT AATTTCTATG CCTGGAAGAG GATGGAGGTC     300
241   GGGCAGCAGG CCGTAGAAGT CTGGCAGGGC CTGGCCCTGC TGTCGGAAGC TGTCCTGCGG     360
301   GGCCAGGCCC TGTTGGTCAA CTCTTCCCAG CCGTGGGAGC CCCTGCAGCT GCATGTGGAT     420
361   AAAGCCGTCA GTGGCCTTCG CAGCCTCACC ACTCTGCTTC GGGCTCTGGG AGCCCAGAAG     480
421   GAAGCCATCT CCCCTCCAGA TGCGGCCTCA GCTGCTCCAC TCCGAACAAT CACTGCTGAC     540
481   ACTTTCCGCA AACTCTTCCG AGTCTACTCC AATTTCCTCC GGGGAAAGCT GAAGCTGTAC     600
541   ACAGGGGAGG CCTGCAGGAC AGGGGACAGA TGACcaggtg tgtccacctg ggcatatcca     660
601   ccacctccct caccaacatt gcttgtgcca cacccteccc cgccactcct gaacccgtc      720
661   gaggggctct cagctcagcg ccagcctgtc ccatggacac tccagtgcca gcaatgacat    780
721   ctcaggggcc agaggaactg tccagagagc aactctgaga tct                      823
                   10         20         30         40         50         60
```

FIG. 1

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 823 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TGGTCACCCG GCGCGCCCCA GGTCGCTGAG GGACCCCGGC CAGGCGCGGA GATGGGGGTG      60

CACGAATGTC CTGCCTGGCT GTGGCTTCTC CTGTCCCTGC TGTCGCTCCC TCTGGGCCTC     120

CCAGTCCTGG GCGCCCCACC ACGCCTCATC TGTGACAGCC GAGTCCTGGA GAGGTACCTC     180

TTGGAGGCCA AGGAGGCCGA GAATATCACG ACGGGCTGTG CTGAACACTG CAGCTTGAAT     240
```

-continued

| | | | | | |
|---|---|---|---|---|---|
| GAGAATATCA | CTGTCCCAGA | CACCAAAGTT | AATTTCTATG | CCTGGAAGAG | GATGGAGGTC | 300 |
| GGGCAGCAGG | CCGTAGAAGT | CTGGCAGGGC | CTGGCCCTGC | TGTCGGAAGC | TGTCCTGCGG | 360 |
| GGCCAGGCCC | TGTTGGTCAA | CTCTTCCCAG | CCGTGGGAGC | CCCTGCAGCT | GCATGTGGAT | 420 |
| AAAGCCGTCA | GTGGCCTTCG | CAGCCTCACC | ACTCTGCTTC | GGGCTCTGGG | AGCCCAGAAG | 480 |
| GAAGCCATCT | CCCCTCCAGA | TGCGGCCTCA | GCTGCTCCAC | TCCGAACAAT | CACTGCTGAC | 540 |
| ACTTTCCGCA | AACTCTTCCG | AGTCTACTCC | AATTTCCTCC | GGGGAAAGCT | GAAGCTGTAC | 600 |
| ACAGGGGAGG | CCTGCAGGAC | AGGGGACAGA | TGACCAGGTG | TGTCCACCTG | GGCATATCCA | 660 |
| CCACCTCCCT | CACCAACATT | GCTTGTGCCA | CACCCTCCCC | CGCCACTCCT | GAACCCCGTC | 720 |
| GAGGGGCTCT | CAGCTCAGCG | CCAGCCTGTC | CCATGGACAC | TCCAGTGCCA | GCAATGACAT | 780 |
| CTCAGGGGCC | AGAGGAACTG | TCCAGAGAGC | AACTCTGAGA | TCT | | 823 |

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGCAGCTGCC TGCA                                                                            14

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAAGGCGCGC CTTC                                                                             14

( 2 ) INFORMATION FOR SEQ ID NO:4:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCGGCCGCAC GCGTACGTAC CGGTTCGAAG CGCGCACGGC CGACCATGGT TAACTCCGGA    60

CACGTGCGGA CCGCGGCCGC                                                      80

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

AAAATTCGAA CCTGGGGAGA AACCAGAG                                                                     28

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GTTTCCCCGC GAATGGACAA GCTTAAAA                                                                     28

( 2 ) INFORMATION FOR SEQ ID NO:7:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GCGGCCGCAC GCGTGAGCTC CGCGGTTCGA ATCCGGGAT TCGAACATCG ATAAAAGATC     60

TACGTAGGTA ACCACGTGCG GACCGAGCGG CCGC                                94

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGCCGGGAAC GGTGCATT                                                                                18

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GGGCAAGGGG GTGGGCCTAT A                                                                            21

( 2 ) INFORMATION FOR SEQ ID NO:10:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

ATCGATTGAA TTCCCCGGGG ATCCTCTAGA GTCGACCTGC AGAAGCTTGC TCTCGAGCAG     60

CGCTGCTCGA GAGATCT                                                   77

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCTAGGCGC CACCATGGGG GTGC        24

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGCGCCCTG CAGGACATGT        20

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCGGCCGCAG GAACCCTAG TGATGGAGTT GG        32

TREATING ANEMIA USING RECOMBINANT ADENO-ASSOCIATED VIRUS VIRIONS COMPRISING AN EPO DNA SEQUENCE

CROSS-REFERENCE TO RELATED APPLICATION

This application is a continuation-in-part of U.S. application Ser. No. 08/588,355, filed Jan. 18, 1996, from which priority is claimed pursuant to 35 USC §120 and which is incorporated herein by reference in its entirety.

TECHNICAL FIELD

The present invention relates generally to DNA delivery methods. More particularly, the invention relates to the use of recombinant adeno-associated virus (AAV) virions for in vitro and in vivo delivery of erythropoietin (EPO) to muscle cells and tissue for the treatment of anemia. The method provides for sustained, high-level expression of EPO.

BACKGROUND OF THE INVENTION

The production of red blood cells in mammals, erythropoiesis, is under the control of the hormone erythropoietin (EPO). EPO is normally present in low concentrations in plasma, where it is sufficient to maintain equilibrium between normal blood cell loss (i.e., through aging) and red blood cell production.

Anemia is a decrease in red blood cell mass caused by decreased production or increased destruction of red blood cells. EPO is currently used for treatment of the anemias associated with end-stage renal failure and acquired immunodeficiency syndrome (AIDS), particularly in subjects who are being treated with zidovudine (AZT). EPO is also used for amelioration of the anemia associated with cancer chemotherapy.

Another group of anemic disorders, each of which results from an inherited abnormality in globin production, is termed the hemoglobinopathies. Hemoglobinopathies include a spectrum of disorders that can be classified broadly into two types. The first type are those that result from an inherited structural alteration in one of the globin chains, for example sickle cell anemia. These disorders give rise to the production of abnormal hemoglobin molecules. The second major subdivision of hemoglobinopathies, the thalassemias, results from inherited defects in the rate of synthesis of one or more of the globin chains. This causes ineffective erythropoiesis, hemolysis, and varying degrees of anemia due to the inadequate production of red blood cells. Accordingly, EPO can be used in the treatment of anemias, for example, hemoglobinopathies which are characterized by low or defective red blood cell production and/or increased red blood cell destruction.

β-thalassemia is a common single gene disorder arising from approximately 100 different mutations of the beta globin gene locus. Weatherall, D. J. (1994) in *The Molecular Basis of Blood Diseases*, Second Edition, Stamatoyannopoulos et al. eds., pages 157–205: WB Saunders, Philadelphia, Pa. The condition affects more than one million people worldwide. Current clinical management of severely anemic thalassemic patients generally involves transfusion with normal-matched donor blood, splenectomy, and other measures that help prolong circulating red blood cell survival. Schwartz et al. (1991) "The thalassemia syndromes," in *Hematology: Basic Principals and Practice*, First Edition, Hoffman et al. eds., pages 368–392, Churchill Livingstone, New York, N.Y.

Sickle cell anemia is a condition resulting from the production of abnormal β-globin molecules due to an inherited mutation in the β-globin gene. The mutation results in the substitution of valine for glutamic acid in the β6 position of the molecule. Individuals homozygous for the abnormal β-globin gene ($\beta^S$) are symptomatic. Additionally, individuals heterozygous for $\beta^S$ and heterozygous for other abnormal β-globin genes, for example, the $\beta^C$ gene or for β-thalassemia, may also have symptoms of sickle cell anemia. Manifestations of the disease are due to the fact that, under certain physiologic conditions, the abnormal hemoglobin molecule (HbS) polymerizes, resulting in "sickling" of red blood cells. The consequences of sickling of red blood cells are increased cell destruction, resulting in anemia, and blockage in capillary beds which can result in damage to a number of organs such as the kidney, spleen, lung, bones and eyes.

Recent advances in molecular biology have led to an understanding of the molecular interactions between the various globin chains and, based on this knowledge, pharmacological treatment using butyrate, chotrimazole, or hydroxyurea (De Franceschi et al. (1996) *Blood* 87:1188–1195; Sauvage et al. (1993) *Br. J. Haematol.* 84:492) to increase globin concentration has been used in short-term clinical trials in small numbers of thalassemic patients to varying degrees of success. Olivieri et al. (1992) *Blood* 80:3258; Rachmilewitz et al. (1991) *Blood* 78:1145. The use of these pharmacological agents can mitigate the chain imbalance in beta-thalassemia and the precipitation of sickle hemoglobin in patients with sickle cell anemia. In a much smaller population of thalassemic patients, bone marrow transplantation of matched marrow has been shown to be curative (Thomas et al. (1982) *Lancet* 2:227–229; Lucarelli et al. (1990) *N. Engl. J. Med.* 322:417–421), however, this approach is only available to a limited number of patients. Since each of these approaches benefit only a few patients and carry the risk of substantial side effects, including death, novel therapeutic strategies are needed.

One new therapeutic approach for the treatment of thalassemia involves the delivery of high levels of systemic erythropoietin (EPO) to patients in order to increase red blood cell mass and survival. Administration of human EPO has been shown to transiently increase levels of erythropoieis and circulating red blood cell mass in rodents, normal primates, and in a small number of experimental studies with human patients. Al-Khatti et al. (1988) *Trans. Assoc. Am. Physicians* 101:54–61; Nagel et al. (1993) *Blood* 81:9–14; Olivieri et al. (1992) *Blood* 80:3258; Rachmilewitz et al. (1991) *Blood* 78:1145; Leroy-Viard et al. (1991) *Blood* 78:1596; Al-Khatti et al. (1987) *N. Engl. J. Med.* 317:415.

Administration of high doses of human EPO has shown efficacy in the treatment of sickle cell disease. For example, EPO has been shown to stimulate fetal hemoglobin formation in sickle cell anemia (Al-Khatti et al. (1988) *Trans. Assoc. Am. Physicians* 101:54–61), and some subjects with sickle cell disease who were treated with high doses of EPO responded with increased percentages of F-reticulocytes in peripheral blood (nagel et al. (1993) *Blood* 81:9–14). Further, high doses of EPO with adjunctive hydroxyurea has been shown to improve anemia in several sickle cell patients. Rodgers et al. (1993) *New Engl. J. Med.* 328:73.

Another new therapeutic strategy for the treatment of anemia entails gene therapy of hematopoietic stem cells, wherein transduced-stem cells are used as a reservoir of gene-corrected cells. Williams et al. (1984) *Nature* 310:476–480; Lemischka et al. (1986) *Cell* 45:917–927. In particular, investigators have shown that murine bone marrow, transduced ex vivo by a retroviral vector containing the EPO gene, and then transplanted into lethally-irradiated thalassemic mice, can provide high levels of EPO secretion and improvement in the murine β-thalassemic phenotype in a portion of the reconstituted animals. Villeval et al. (1994) *Blood* 84:928–933. However, several fundamental obstacles prevent gene therapy of hematopoietic stem cells from being realized. These obstacles include: unresolved problems with efficient delivery and integration into quiescent stem cells (Mulligan, R. C. (1993) *Science* 260:926–932); vector design and stability (Takekoshi et al. (1995) *Proc. Natl. Acad. Sci. USA* 92:3014–3018); transgene silencing (Challita et al. (1994) *Proc. Natl. Acad. Sci. USA* 91:2567–2571) and efficient engraftment and repopulation of gene-modified stem cells (Kohn et al. (1995) *Nat. Med.* 1:1017–1023).

Other researchers have reported the transduction of myoblast cells with DNA encoding EPO in vitro without using viral vectors, and the subsequent transplantation of the transduced cells into a murine host. International Patent Publication WO 95/13376, published 18 May 1995. Yet further research has explored ex vivo transduction of cells using adenovirus vectors. The transduced cells are then used to form a matrix (an "organoid") which is surgically implanted in the peritoneal cavity to secrete EPO. Naffakh et al. (1995) *Proc. Natl. Acad. Sci. USA* 92:3194–3198; Descamps et al. (1995) *Gene Ther.* 2:411–417. However, these methods have failed to provide for adequate levels of expression of EPO, for sufficient duration, in treated subjects, and are thus impractical.

Accordingly, the sustained delivery of high levels of EPO would be desirable in the treatment of hemoglobinopathies such as thalassemia and sickle cell disease. Further, the use of gene delivery methods that target cells other than hematopoietic stem cells, and avoid the problems with prior methods, would also be desirable.

Several experimenters have demonstrated the ability to deliver genes to muscle cells with the subsequent systemic circulation of proteins encoded by the delivered genes. See, e.g., Wolff et al. (1990) *Science* 247:1465–1468; Acsadi et al. (1991) *Nature* 352:815–818; Barr and Leiden (1991) *Science* 254:1507–1509; Dhawan et al. (1991) *Science* 254:1509–1512; Wolff et al. (1992) *Human Mol. Genet.* 1:363–369; Eyal et al. (1993) *Proc. Natl. Acad. Sci. USA* 90:4523–4527; Davis et al. (1993) *Hum. Gene Therapy* 4:151–159.

Genes have been delivered to muscle by direct injection of plasmid DNA. Wolff et al. (1990) *Science* 247:1465–1468; Acsadi et al. (1991) *Nature* 352:815–818; Barr and Leiden (1991) *Science* 254:1507–1509. However, this mode of administration generally results in sustained but low levels of expression. Low, but sustained expression levels, may be effective in certain situations, such as for providing immunity, but are generally not desirable for phenotypic improvement in most therapeutic methods.

Viral based systems have also been used for gene delivery to muscle. For example, human adenoviruses are double-stranded DNA viruses which enter cells by receptor-mediated endocytosis. These viruses have been considered well suited for gene transfer because they are easy to grow and manipulate, and they exhibit a broad host range in vivo and in vitro. Adenoviruses are able to infect quiescent as well as replicating target cells and persist extrachromosomally, rather than integrating into the host genome.

Despite these advantages, adenovirus vectors suffer from several drawbacks which make them ineffective for long term gene therapy. In particular, adenovirus vectors express viral proteins that may elicit an immune response which may decrease the life of the transduced cell. This immune reaction may preclude subsequent treatments because of humoral and/or T cell responses. Furthermore, the adult muscle cell may lack the receptor which recognizes adenovirus vectors, precluding efficient transduction of this cell type using such vectors. Thus, attempts to use adenoviral vectors for the delivery of genes to muscle cells has resulted in poor and/or transitory expression. See, e.g., Quantin et al. (1992) *Proc. Natl. Acad. Sci. USA* 89:2581–2584; Acsadi et al. (1994) *Hum. Mol. Genetics* 3:579–584; Acsadi et al. (1994) *Gene Therapy* 1:338–340; Dai et al. (1995) *Proc. Natl. Acad. Sci. USA* 92:1401–1405; Descamps et al. (1995) *Gene Therapy* 2:411–417; Gilgenkrantz et al. (1995) *Hum. Gene Therapy* 6:1265–1274.

Gene therapy methods based upon surgical transplantation of myoblasts has also been attempted. See, e.g., International Publication No. WO 95/13376; Dhawan et al. (1991) *Science* 254:1509–1512; Wolff et al. (1992) *Human Mol. Genet.* 1:363–369; Dai et al. (1992) *Proc. Natl. Acad. Sci. USA* 89:10892–10895; Hamamori et al. (1994) *Hum. Gene Therapy* 5:1349–1356; Hamamori et al. (1995) *J. Clin. Invest.* 95:1808–1813; Blau and Springer (1995) *New Eng. J. Med.* 333:1204–1207; Leiden, J. M. (1995) *New Eng. J. Med.* 333:871–872; Mendell et al. (1995) *New Eng. J. Med.* 333:832–838; and Blau and Springer (1995) *New Eng. J. Med.* 333:1554–1556. However, such methods require substantial tissue culture manipulation and surgical expertise, and, at best, show inconclusive efficacy in clinical trials. Thus, a simple and effective method of gene delivery to muscle, resulting in long-term expression of the delivered gene, would be desirable.

Recombinant vectors derived from an adeno-associated virus (AAV) have been used for gene delivery. AAV is a helper-dependent DNA parvovirus which belongs to the genus Dependovirus. AAV requires infection with an unrelated helper virus, such as adenovirus, a herpesvirus or vaccinia, in order for a productive infection to occur. The helper virus supplies accessory functions that are necessary for most steps in AAV replication. In the absence of such infection, AAV establishes a latent state by insertion of its genome into a host cell chromosome. Subsequent infection by a helper virus rescues the integrated copy which can then replicate to produce infectious viral progeny. AAV has a wide host range and is able to replicate in cells from any species so long as there is also a successful infection of such cells with a suitable helper virus. Thus, for example, human AAV will replicate in canine cells coinfected with a canine adenovirus. AAV has not been associated with any human or animal disease and does not appear to alter the biological properties of the host cell upon integration. For a review of AAV, see, e.g., Berns and Bohenzky (1987) *Advances in Virus Research* (Academic Press, Inc.) 32:243–307.

The AAV genome is composed of a linear, single-stranded DNA molecule which contains approximately 4681 bases (Berns and Bohenzky, supra). The genome includes inverted terminal repeats (ITRs) at each end which function in cis as origins of DNA replication and as packaging signals for the virus. The internal nonrepeated portion of the genome includes two large open reading frames, known as the AAV rep and cap regions, respectively. These regions code for the viral proteins involved in replication and packaging of the virion. For a detailed description of the AAV genome, see, e.g., Muzyczka, N. (1992) *Current Topics in Microbiol. and Immunol.* 158:97–129.

The construction of recombinant AAV (rAAV) virions has been described. See, e.g., U.S. Pat. Nos. 5,173,414 and 5,139,941; International Publication Numbers WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines 90* (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; and Kotin, R. M. (1994) *Human Gene Therapy* 5:793–801.

Recombinant AAV virion production generally involves cotransfection of a producer cell with an AAV vector plasmid and a helper construct which provides AAV helper functions to complement functions missing from the AAV vector plasmid. In this manner, the producer cell is capable of expressing the AAV proteins necessary for AAV replication and packaging. The AAV vector plasmid will include the DNA of interest flanked by AAV ITRs which provide for AAV replication and packaging functions. AAV helper functions can be provided via an AAV helper plasmid that includes the AAV rep and/or cap coding regions but which lacks the AAV ITRs. Accordingly, the helper plasmid can neither replicate nor package itself. The producer cell is then infected with a helper virus to provide accessory functions, or with a vector which includes the necessary accessory functions. The helper virus transactivates the AAV promoters present on the helper plasmid that direct the transcription and translation of AAV rep and cap regions. Upon subsequent culture of the producer cells, recombinant AAV virions harboring the DNA of interest, are produced.

Recombinant AAV virions have been shown to exhibit tropism for respiratory epithelial cells (Flotte et al. (1992) *Am. J. Respir. Cell Mol. Biol.* 7:349–356; Flotte et al. (1993) *J. Biol. Chem.* 268:3781–3790; Flotte et al. (1993) *Proc. Natl. Acad. Sci. USA* 90:10613–10617) and neurons of the central nervous system (Kaplitt et al. (1994) *Nature Genetics* 8:148–154). These cell types are well-differentiated, slowly-dividing or postmitotic. Flotte et al. (1993) *Proc. Natl. Acad. Sci. USA* 90:10613–10617; Kaplitt et al. (1994) *Nature Genetics* 8:148–154. The ability of AAV vectors to transduce nonproliferating cells (Podsakoff et al. (1994) *J. Virol.* 68:5656–5666; Russell et al. (1994) *Proc. Natl. Acad. Sci. USA* 91:8915–8919; Flotte et al. (1994) *Am. J. Respir. Cell Mol. Biol.* 11:517–521) along with the attributes of being inherently defective and nonpathogenic, place AAV in a unique position among gene therapy viral vectors.

Despite these advantages, the use of recombinant AAV virions to deliver the EPO gene to muscle cells in vivo has not heretofore been disclosed, particularly in the context of treating anemia in mammalian subjects.

SUMMARY OF THE INVENTION

Accordingly, the present invention is based on the surprising and unexpected discovery that recombinant AAV (rAAV) virions provide for efficient delivery of the EPO gene and sustained production of EPO in muscle cells. Recombinant AAV virions allow delivery of DNA directly to muscle tissue. Thus, EPO can be produced and secreted in vivo from transduced muscle cells such that systemic delivery of therapeutic levels of EPO is achieved. Transduction can be carried out using both in vivo and in vitro modes of DNA delivery. The ability to deliver and express nucleotide sequences encoding EPO in muscle cells, as well as to provide for secretion of EPO from transduced cells, allows the use of gene therapy approaches to treat anemia.

Furthermore, the ability to deliver DNA to muscle cells by intramuscular administration in vivo provides a more efficient and convenient method of gene transfer.

Thus, in one embodiment, the invention relates to a method of treating anemia in a mammalian subject which entails introducing into a muscle cell or tissue of said subject in vivo a therapeutically effective amount of a pharmaceutical composition which comprises (a) a pharmaceutically acceptable excipient; and (b) recombinant AAV virions which comprise an AAV vector containing a nucleic acid molecule encoding EPO operably linked to control elements that direct the transcription and translation thereof when present in the subject. Preferably, the nucleic acid molecule encodes native EPO.

In related embodiments, the method further entails coupling delivery of the rAAV virions with adjunctive pharmacological therapies that also serve to increase hematocrit in mammalian subjects having anemic disorders.

In another embodiment, the invention is directed to a method of treating thalassemia in a mammalian subject which entails introducing a recombinant AAV virion into a muscle cell or tissue in vitro to produce a transduced muscle cell, and then administering a therapeutically effective amount of a composition to the subject that comprises a pharmaceutically acceptable excipient and the transduced muscle cells or tissue. The recombinant AAV virion used in the method comprises an AAV vector having a nucleic acid molecule that encodes EPO operably linked to control elements capable of directing the transcription and translation thereof following transduction of the subject's cells.

In a further embodiment, the invention relates to an in vivo method to achieve a therapeutically effective amount of systemic EPO in a mammalian subject. The method entails delivering to muscle cells or tissue of the subject a pharmaceutical composition comprising a pharmaceutically acceptable excipient and recombinant AAV virions containing a nucleic acid molecule encoding EPO. The nucleic acid molecule is operably linked to control elements that direct the transcription and translation thereof following transduction of the subject's cells.

In yet other embodiments, the invention is directed to a method for achieving a therapeutically effective amount of systemic EPO in a mammalian subject that entails the steps: (a) introducing a recombinant AAV virion into a muscle cell or tissue in vitro to produce a transduced muscle cell, wherein the recombinant AAV virion comprises an AAV vector having a nucleic acid molecule encoding EPO operably linked to control elements that direct the transcription and translation thereof following transduction of the subject's cells; and (b) administering to the subject a therapeutically effective amount of a composition comprising the transduced cells obtained in step (a).

These and other embodiments of the subject invention will readily occur to those of ordinary skill in the art in view of the disclosure herein.

BRIEF DESCRIPTION OF THE FIGURES

FIG. 1 depicts the nucleotide sequence for human EPO CDNA (SEQ ID NO.:1).

DETAILED DESCRIPTION OF THE INVENTION

Figure 2:
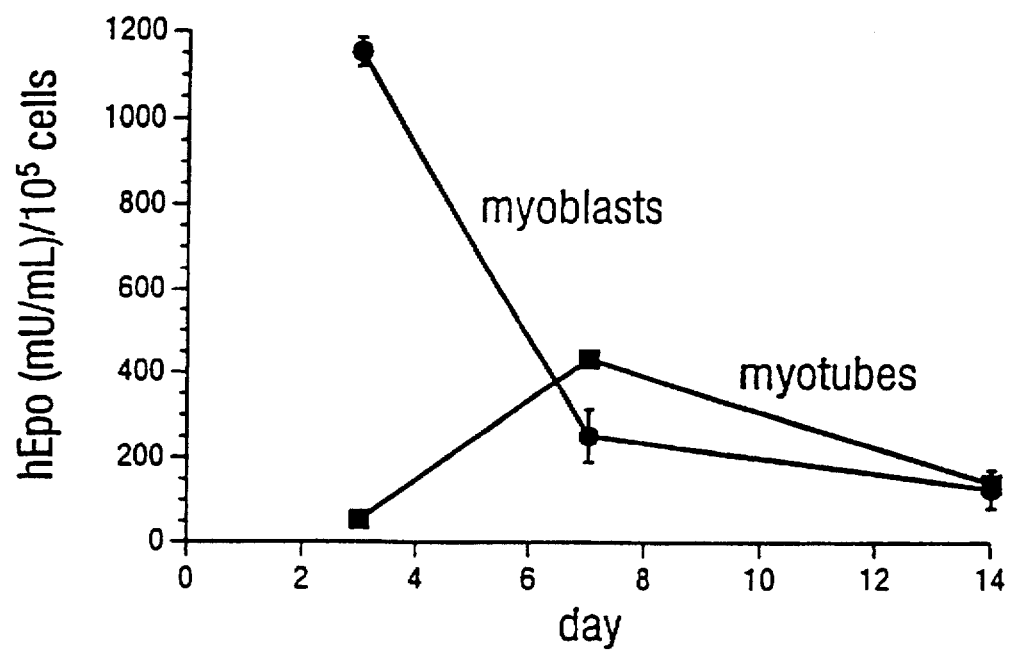
FIG. 2 shows the secretion of human erythropoietin (hEPO) from transduced myotubes and myoblasts, as described in Example 1. Myotubes (differentiated cells) or myoblasts (actively dividing cells) were transduced with rAAV-hEPO at a ratio of approximately $10^5$ per target cell. Levels of secreted hEPO were analyzed in supernatants at various time points. Baseline levels of hEPO, prior to transduction, were below the level of detection in both cell populations; the values at each time point represent replicate values +/− standard deviation.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

As used herein, the term "thalassemia" encompasses hereditary anemias that occur due to mutations affecting the synthesis of hemoglobin. Thus, the term includes any symptomatic anemia resulting from thalassemic conditions such as severe or β-thalassemia, thalassemia major, thalassemia intermedia, α-thalassemias such as hemoglobin H disease, and the like.

The term "sickle cell anemia" or "sickle cell disease" is defined herein to include any symptomatic anemic condition which results from sickling of red blood cells. Manifestations of sickle cell disease include: anemia; pain; and/or organ dysfunction, such as renal failure, retinopathy, acute-chest syndrome, ischemia, priapism and stroke.

The term "gene delivery" or "gene transfer" refers to methods or systems for reliably inserting foreign DNA into target cells, such as into muscle cells. Such methods can result in transient or long term expression of genes. Gene transfer provides a unique approach for the treatment of acquired and inherited diseases. A number of systems have been developed for gene transfer into mammalian cells. See, e.g., U.S. Pat. No. 5,399,346.

"Erythropoietin," or "EPO," is a glycoprotein hormone produced in fetal liver and adult kidney which acts on progenitor cells in the bone marrow and other hematopoietic tissue to stimulate the formation of red blood cells. Genes encoding human and other mammalian EPO have been cloned, sequenced and expressed, and show a high degree of sequence homology in the coding region across species. Wen et al. (1993) *Blood* 82:1507–1516. The sequence of the gene encoding native human EPO, as well as methods of obtaining the same, are described in, e.g., U.S. Pat. Nos. 4,954,437 and 4,703,008, incorporated herein by reference in their entirety, as well as in Jacobs et al. (1985) *Nature* 313:806–810; Lin et al. (1985) *Proc. Natl. Acad. Sci. USA* 82:7580; International Publication Number WO 85/02610; and European Patent Publication Number 232,034 B1. In addition, the sequences of the genes encoding native feline, canine and porcine EPO are known and readily available (GenBank Accession Nos.: L10606; L13027; and L10607, respectively), and the sequence of the gene encoding monkey (*Macaca mulatta*) is also known and available (GenBank Accession No.: L10609). The term "EPO" as used herein refers to the native, full-length secreted form of EPO, as well as to analogs or derivatives thereof comprising single or multiple amino acid substitutions, deletions or additions which retain EPO function or activity. In this regard, a number of small peptides have been identified which bind to and activate the receptor for EPO. Wrighton et al. (1996) *Science* 273:458–463; Livnah et al. (1996) *Science* 273:464–471. Thus, recombinant AAV virions described herein which include a nucleic acid molecule encoding EPO, or encoding an analog or derivative thereof having EPO activity, are useful in the treatment of blood disorders characterized by defective red blood cell formation, such as in the treatment of anemia. Increased red blood cell production due to the production of EPO can be readily determined by an appropriate indicator, such as by comparing hematocrit measurements pre- and post-treatment, measuring increases in red blood cell count, hemoglobin concentration, or in reticulocyte counts.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes (described below), but retain functional flanking ITR sequences (also described below). Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

By "recombinant virus" is meant a virus that has been genetically altered, e.g., by the addition or insertion of a heterologous nucleic acid construct into the particle.

By "AAV virion" is meant a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a DNA molecule of interest which is flanked on both sides by AAV ITRs. An rAAV virion is produced in a suitable producer cell which has had an AAV vector, AAV helper functions and accessory functions introduced therein. In this manner, the producer cell is rendered capable of encoding AAV polypeptides that are required for packaging the AAV vector (containing a recombinant nucleotide sequence of interest) into recombinant virion particles for subsequent gene delivery.

The term "transfection" is used to refer to the uptake of foreign DNA by a mammalian cell. A cell has been "transfected" when exogenous DNA has been introduced inside the cell membrane. A number of transfection techniques are known in the art. See, e.g., Graham et al. (1973) *Virology*, 52:456, Sambrook et al. (1989) Molecular Cloning, a laboratory manual, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties, such as a plasmid vector and other nucleic acid molecules, into suitable cells. The term refers to both stable and transient uptake of the genetic material.

The term "transduction" denotes the delivery of a DNA molecule to a recipient cell either in vivo or in vitro, via a replication-defective viral vector, such as via a recombinant AAV virion.

By "muscle cell" or "tissue" is meant a cell or group of cells derived from muscle, including but not limited to cells and tissue derived from skeletal muscle; smooth muscle, e.g., from the digestive tract, urinary bladder and blood vessels; and cardiac muscle. The term captures muscle cells both in vitro and in vivo. Thus, for example, an isolated cardiomyocyte would constitute a "muscle cell" for purposes of the present invention, as would a muscle cell as it exists in muscle tissue present in a subject in vivo. The term also encompasses both differentiated and nondifferentiated muscle cells, such as myocytes, myotubes, myoblasts, cardiomyocytes and cardiomyoblasts.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct in which the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

By "DNA" is meant a polymeric form of deoxyribonucleotides (adenine, guanine, thymine, or cytosine) in doublestranded or single-stranded form, either relaxed and supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence homologous to the mRNA). The term captures molecules that include the four bases adenine, guanine, thymine, or cytosine, as well as molecules that include base analogues which are known in the art.

A "gene" or "coding sequence" or a sequence which "encodes" a particular protein, is a nucleic acid molecule which is transcribed (in the case of DNA) and translated (in the case of mRNA) into a polypeptide in vitro or in vivo when placed under the control of appropriate regulatory sequences. The boundaries of the gene are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

By "mammalian subject" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

B. General Methods

The present invention provides for the treatment of anemia in a mammalian subject by transfer of a nucleic acid molecule encoding EPO into a muscle cell of the subject using recombinant AAV virions. The method allows for the direct, in vivo injection of recombinant AAV virions into muscle tissue, e.g., by intramuscular injection, as well as for the in vitro transduction of muscle cells which can subsequently be introduced into a subject for treatment. The invention also provides for secretion of EPO in vivo, from transduced muscle cells, such that systemic circulation can be achieved.

Muscle provides a desirable target for gene therapy since muscle cells are readily accessible and nondividing. However, the present invention also finds use with nondifferentiated muscle cells, such as myoblasts, which can be transduced in vitro, and subsequently introduced into a subject.

Since muscle has ready access to the circulatory system, EPO produced and secreted by muscle cells and tissue in vivo will enter the bloodstream for systemic delivery. Furthermore, since sustained, therapeutic levels of EPO secretion from muscle is achieved in vivo using the present invention, repeated parenteral delivery is avoided or reduced in frequency such that therapy can be accomplished using only one or few injections. Thus, the present invention provides significant advantages over prior methods of treating anemia.

The recombinant AAV virions of the present invention, including a nucleotide sequence encoding EPO, can be produced using standard methodology, known to those of skill in the art. The methods generally involve the steps of (1) introducing an AAV expression vector into a suitable producer cell; (2) introducing an AAV helper construct into the producer cell, where the helper construct includes AAV coding regions capable of being expressed in the cell to complement AAV helper functions missing from the AAV vector; (3) introducing one or more helper viruses and/or accessory function vectors into the producer cell, wherein the helper virus and/or accessory function vectors provide accessory functions capable of supporting efficient recombinant AAV ("rAAV") virion production in the cell; and (4) culturing the producer cell to produce rAAV virions. The AAV expression vector, AAV helper construct and the helper virus or accessory function vector(s) can be introduced into the producer cell, either simultaneously or serially, using standard transfection techniques.

1. AAV Expression Vectors

AAV expression vectors are constructed using known techniques to at least provide as operatively linked components in the direction of transcription, control elements including a transcriptional initiation region, the nucleotide sequence encoding erythropoietin, and a transcriptional termination region. The control elements are selected to be functional in a mammalian muscle cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAVX7, etc. Furthermore, 5' and 3' ITRs which flank the selected nucleotide sequence in an AAV expression vector need not necessarily be identical or derived from the same AAV serotype or isolate, so long as they function as intended, i.e., to allow for packaging of virions.

In the practice of the invention, a nucleotide sequence encoding EPO is used. The sequence of the human EPO gene, as well as methods of obtaining the same, have been previously described (U.S. Pat. No. 4,954,437; Jacobs et al. (1985) *Nature* 313:806–810; Lin et al. (1985) *Proc. Natl. Acad. Sci. USA* 82:7580; International Publication Number WO 85/02610; and European Patent Publication Number 232,034 B1). The sequences for feline, canine, porcine and monkey EPO are also known (GenBank Accession Nos.: L10606; L13027; L10607; and L10609, respectively). The recombinant AAV virions described herein include a nucleotide sequence encoding a mammalian EPO, or encoding an analog or derivative thereof having EPO activity.

The nucleotide sequence encoding EPO is operably linked to control elements that direct the transcription or expression thereof in the subject in vivo. Such control elements can comprise control sequences normally associated with an EPO gene. Alternatively, heterologous control sequences can be employed. Useful heterologous control sequences generally include those derived from sequences encoding mammalian or viral genes. Examples include, but are not limited to, the SV40 early promoter; mouse mammary tumor virus LTR promoter; adenovirus major late promoter (Ad MLP); herpes simplex virus (HSV) promoters; a cytomegalovirus (CMV) promoter such as the CMV immediate early promoter region (CMV-IE promoter); a rous sarcoma virus (RSV) promoter; synthetic promoters; hybrid promoters; and the like. In addition, sequences derived from nonviral genes, such as the murine metallothionein gene, will also find use herein. Such promoter sequences are commercially available from, e.g., Stratagene (San Diego, Calif.).

For purposes of the present invention, control elements, such as muscle-specific and inducible promoters, enhancers and the like, will be of particular use. Such control elements include, but are not limited to, those derived from the actin and myosin gene families, such as from the myoD gene family (Weintraub et al. (1991) *Science* 251:761–766); the myocyte-specific enhancer binding factor MEF-2 (Cserjesi and Olson (1991) *Mol. Cell Biol.* 11:4854–4862); control elements derived from the human skeletal actin gene (Muscat et al. (1987) *Mol. Cell Biol.* 7:4089–4099) and the cardiac actin gene; muscle creatine kinase sequence elements (Johnson et al. (1989) *Mol. Cell Biol.* 9:3393–3399) and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors (Semenza et al. (1991) *Proc. Natl. Acad. Sci. USA* 88:5680–5684; Semenza et al. *J. Biol. Chem.* 269:23757–23763); steroid-inducible elements and promoters, such as the glucocorticoid response element (GRE) (Mader and White (1993) *Proc. Natl. Acad. Sci. USA* 90:5603–5607); the fusion consensus element for RU486 induction; elements that provide for tetracycline regulated gene expression (Dhawan et al. (1995) *Somat. Cell. Mol. Genet.* 21:233–240; Shockett et al. (1995) *Proc. Natl. Acad. Sci. USA* 92:6522–6526; and inducible, synthetic humanized promoters (Rivera et al. (1996) *Nature Med.* 2:1028–1032).

These and other regulatory elements can be tested for potential in vivo efficacy using the in vitro myoblast model, which mimics quiescent in vivo muscle physiology, described in the examples below.

The AAV expression vector which harbors EPO DNA bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Alternatively, AAV ITRs can be excised from the viral genome or from an AAV vector containing the same and fused 5' and 3' of a selected nucleic acid construct containing EPO coding sequences present in another vector using standard ligation techniques, such as those described in Sambrook et al., supra. For example, ligations can be accomplished in 20 mM Tris-Cl pH 7.5, 10 mM $MgCl_2$, 10 mM DTT, 33 µg/ml BSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 µg/ml total DNA concentrations (5–100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian muscle cells can be used. The complete chimeric sequence is assembled from overlapping oligonucleotides prepared by standard methods. See, e.g., Edge, *Nature* (1981) 292:756; Nambair et al. *Science* (1984) 223:1299; Jay et al. *J. Biol. Chem.* (1984) 259:6311.

In order to produce rAAV virions, an AAV expression vector is introduced into a suitable producer cell using known techniques, such as by transfection. A number of transfection techniques are generally known in the art. See, e.g., Graham et al. (1973) *Virology* 52:456, Sambrook et al. (1989) *Molecular Cloning*, a laboratory manual, Cold Spring Harbor Laboratories, New York. Davis et al. (1986) *Basic Methods in Molecular Biology*, Elsevier, and Chu et al. (1981) *Gene* 13:197. Particularly suitable transfection methods include calcium phosphate co-precipitation (Graham et al. (1973) *Virol.* 52:456–467), direct micro-injection into cultured cells (Capecchi, M. R. (1980) *Cell* 22:479–488), electroporation (Shigekawa et al. (1988) *BioTechniques* 6:742–751), liposome mediated gene transfer (Mannino et al. (1988) *BioTechniques* 6:682–690), lipid-mediated transduction (Felgner et al. (1987) *Proc. Natl. Acad. Sci. USA* 84:7413–7417), and nucleic acid delivery using high-velocity microprojectiles (Klein et al. (1987) *Nature* 327:70–73).

For the purposes of the invention, suitable cells for producing rAAV virions include microorganisms, yeast cells, insect cells, and mammalian cells, that can be, or have been, used as recipients of a heterologous DNA molecule. The term includes the progeny of the original cell which has been transfected. Thus, a "producer cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

2. AAV Helper Functions

Producer cells containing the above-described AAV expression vectors must be rendered capable of providing AAV helper functions in order to replicate and encapsidate the EPO-encoding nucleotide sequences and associated control sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97–129; and Kotin, R. M. (1994) *Human Gene Therapy* 5:793–801. Suitable homologues of the AAV rep coding region include the human herpesvirus 6 (HHV-6) rep gene which is also known to mediate AAV-2 DNA replication (Thomson et al. (1994) *Virology* 204:304–311).

By "AAV cap coding region" is meant the art-recognized region of the AAV genome which encodes the capsid proteins VP1, VP2, and VP3, or functional homologues thereof. These cap expression products are the capsid proteins which are collectively required for packaging the viral genome. For a description of the AAV cap coding region, see, e.g., Muzyczka, N. and Kotin, R. M. (supra).

AAV helper functions are introduced into the producer cell by transfecting the cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) *J. Virol.* 65:2936–2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

3. Accessory Functions

The producer cell must also be rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

Particularly, accessory functions can be introduced into and then expressed in producer cells using methods known to those of skill in the art. Commonly, accessory functions are provided by infection of the cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241–247; McPherson et al. (1985) *Virology* 147:217–222; Schlehofer et al. (1986) *Virology* 152:110–117.

Alternatively, accessory functions can be provided using an accessory function vector. Accessory function vectors include nucleotide sequences that provide one or more accessory functions. An accessory function vector is capable of being introduced into a suitable producer cell in order to support efficient AAV virion production in the cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a producer cell to provide accessory functions.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses,* vol. I (P. Tijssen, ed.), and Muzyczka, N. (1992) *Curr. Topics. Microbiol. and Immun.* 158:97–129. Specifically, early adenoviral gene regions E1a, E2a, E4, VAI RNA and, possibly, E1b are thought to participate in the accessory process. Janik et al. (1981) *Proc. Natl. Acad. Sci. USA* 78:1925–1929. Herpesvirus-derived accessory functions have been described. See, e.g., Young et al. (1979) *Prog. Med. Virol.* 25:113. Vaccinia virus-derived accessory functions have also been described. See, e.g., Carter, B. J. (1990), supra., Schlehofer et al. (1986) *Virology* 152:110–117.

As a consequence of the infection of the producer cell with a helper virus, or transfection of the cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the producer cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions are then ready for use for DNA delivery, such as in gene therapy applications, for the production of transgenic animals, in vaccination, and particularly for the delivery of genes to a variety of muscle cell types.

4. In vitro and In vivo Delivery of rAAV Virions

Generally, rAAV virions are introduced into a muscle cell using either in vivo or in vitro transduction techniques. If transduced in vitro, the desired recipient muscle cell will be removed from the subject, transduced with rAAV virions and reintroduced into the subject. Alternatively, syngeneic or xenogeneic muscle cells can be used where those cells will not generate an inappropriate immune response in the subject.

Suitable methods for the delivery and introduction of transduced cells into a subject have been described. For example, cells can be transduced in vitro by combining recombinant AAV virions with muscle cells e.g., in appropriate media, and screening for those cells harboring the DNA of interest using conventional techniques such as Southern blots and/or PCR, or by using selectable markers. Transduced cells can then be formulated into pharmaceutical compositions, described more fully below, and the composition introduced into the subject by various routes, such as by intramuscular, intravenous, subcutaneous and intraperitoneal injection, or by injection into smooth muscle, using e.g., a catheter.

For in vivo delivery, the rAAV virions will be formulated into pharmaceutical compositions and will generally be administered parenterally, e.g., by intramuscular injection directly into skeletal muscle. Pharmaceutical compositions will comprise sufficient genetic material to produce a therapeutically effective amount of EPO, i.e., an amount sufficient to reduce or ameliorate symptoms of anemia or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

Appropriate doses will depend on the mammal being treated (e.g., human or nonhuman primate or other mammal), age and general condition of the subject to be treated, the severity of the anemic condition being treated, the mode of administration of the rAAV virions, among other factors. An appropriate effective amount can be readily determined by one of skill in the art.

Thus, a "therapeutically effective amount" of rAAV virions will fall in a relatively broad range that can be determined through clinical trials. For example, for in vivo injection, i.e., injection directly to skeletal muscle, a therapeutically effective dose will be on the order of from about $10^6$ to $10^{15}$ of the rAAV virions, more preferably $10^8$ to $10^{14}$.

For in vitro transduction, the amount of transduced cells in the pharmaceutical compositions will be from about $10^4$ to $10^{10}$ muscle cells, more preferably $10^5$ to $10^8$ muscle cells. An effective amount of rAAV virions to be delivered to muscle cells in vitro will be on the order of $10^8$ to $10^{13}$ rAAV virions. When the transduced cells are introduced to vascular smooth muscle, a lower dose may be appropriate. Other effective dosages can be readily established by one of ordinary skill in the art through routine trials establishing dose response curves.

"Therapeutically effective levels" of systemic EPO in a treated mammalian subject will generally fall within the range of 1 to 10,000 mU/mL EPO. Appropriate levels will of course depend on the mammal being treated, the nature and severity of the anemic condition being treated, and the age and general health of the subject.

Dosage treatment may be a single dose schedule or a multiple dose schedule. In this regard, it has been shown by the experimental studies which follow, that sustained, therapeutically effective levels of EPO can be provided in treated subjects using a single administration of the rAAV virions. However, the subject may be administered as many doses as appropriate. One of skill in the art can readily determine an appropriate number of doses, and monitor therapeutic benefit using the methods described above.

The in vitro or in vivo delivery of rAAV virions can also be coupled with adjunctive pharmacological therapies suitable for effectively increasing globin concentration in a treated subject. Such treatments include administration of therapeutically effective amounts of butyrate, clotrimazole, or hydroxyurea as previously described. De Franceschi et al. (1996) *Blood* 87:1188–1195; Sauvage et al. (1993) *Br. J. Haematol.* 84:492; Olivieri et al. (1992) *Blood* 80:3258; Rachmilewitz et al. (1991) *Blood* 78:1145. Use of such pharmacological agents helps mitigate chain imbalance in β-thalassemia, and can be used in combination with delivery of EPO-encoding rAAV virions to "balance" erythroid expansion in treated subjects. Rodgers (1993) *N. Engl. J. Med.* 328:73. Appropriate dosages of the adjunctive agents are generally known and have been reported in the art (Rodgers, G. P. (1994) "Pharmacologic Modulation of Fetal Hemoglobin," in *Sickle Cell Disease; Basic Principals and Clinical Practice*, Embury et al. eds., Raven Press, Ltd., New York, N.Y.), and can thus readily be determined by those skilled in the art.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Vector constructs

A. Construction of p1909adhlacZ.

Plasmid p1909adhlacZ was used as the helper construct in the following examples and was constructed from plasmid pWadhlacZ. Plasmid pWadhlacZ was constructed by partially digesting plasmid pUC119 (GeneBank Reference Name: U07649, GeneBank Accession Number: U07649) with AflIII and BspHI, blunt-end modifying with the klenow enzyme, and then ligating to form a circular 1732 bp plasmid containing the bacterial origin and the amp gene only (the polylinker and F1 origin was removed). The blunted and ligated AflIII and BspHI junction forms a unique NspI site. The 1732 bp plasmid was cut with NspI, blunt-end modified with T4 polymerase, and a 20 bp HinDIII-HinCII fragment (blunt-end modified with the klenow enzyme) obtained from the pUC119 polylinker was ligated into the blunted NspI site of the plasmid. The HinDIII site from the blunted polylinker was regenerated, and then positioned adjacent to the bacterial origin of replication. The resulting plasmid was then cut at the unique PstI/Sse8387I site, and an Sse8387I-PvuII-Sse8387I oligonucleotide, having the sequence: 5'-GGCAGCTGCCTGCA-3' (SEQ ID NO.:2), was ligated therein. The remaining unique BspHI site was cut, blunt-end modified with klenow enzyme, and an AscI linker oligonucleotide, having the sequence: 5'-GAAGGCGCGCCTTC-3' (SEQ ID No.:3) was ligated therein, eliminating the BspHI site. The resulting plasmid was called pWee.

In order to create the pWadhlacZ construct, a CMVlacZ expression cassette (comprising a nucleotide sequence flanked 5' and 3' by AAV ITRs, containing the following elements: a CMV promoter, the hGH 1st intron, an adhlacz fragment and an SV40 early polyadenylation site) was inserted into the unique PvuII site of pWee using multiple steps such that the CMV promoter was arranged proximal to the bacterial amp gene of pWee.

More particularly, a CMVlacZ expression cassette was derived from the plasmid psub201CMV, which was constructed as follows. An oligonucleotide encoding the restriction enzyme sites:
NotI-MluI-SnaBI-AgeI-BstBI-BssHII-NcoI-HpaI-BspEI-PmlI-RsrII-NotI
and having the following nucleotide sequence:
5'-GCGGCCGCACGCGTACGTACCGGTTCGAAGCG-CGCACGGCCGACCATGGTTAACTCCGG-ACACGTGCGGACCGCGGCCGC-3' (SEQ ID No.:4) was synthesized and cloned into the blunt-end modified KasI-EarI site (partial) of pUC119 to provide a 2757 bp vector fragment. A 653 bp SpeI-SacII fragment containing a nucleotide sequence encoding a CMV immediate early promoter was cloned into the SnaBI site of the 2757 bp vector fragment. Further, a 269 bp PCR-produced BstBI-BstBI fragment containing a nucleotide sequence encoding the hGH 1st intron which was derived using the following primers:
5'-AAATTCGAACCTGGGGAGAAACCAGAG-3' (SEQ ID NO.:5) and
3'-aaaattcgaacaggtaagcgcccctTTG-5' (SEQ ID NO.:6), was cloned into the BstBI site of the 2757 bp vector fragment, and a 135 bp HpaI-BamHI (blunt-end modified) fragment containing the SV40 early polyadenylation site from the pCMV-β plasmid (CLONETECH) was cloned into the HpaI site of the subject vector fragment. The resulting construct was then cut with NotI to provide a first CMV expression cassette.

Plasmid pW1909adhlacZ was constructed as follows. A 4723 bp SpeI-EcoRV fragment containing the AAV rep and cap encoding region was obtained from the plasmid pGN1909 (ATCC Accession Number 69871). The pGN1909 plasmid is a high efficiency AAV helper plasmid having AAV rep and cap genes with an AAV p5 promoter region that is arranged in the construct to be downstream from its normal position (in the wild type AAV genome) relative to the rep coding region. The 4723 bp fragment was blunt-end modified, and AscI linkers were ligated to the blunted ends. The resultant fragment was then ligated into the unique AscI site of pWadhlacZ and oriented such that the AAV coding sequences were arranged proximal to the bacterial origin of replication in the construct.

Plasmid pW1909adhlacZ includes the bacterial beta-galactosidase (β-gal) gene under the transcriptional control of the cytomegalovirus immediate early promoter (CMVIE).

B. Construction of pW1909EPO.

Plasmid pW1909adhlacZ was modified to express human erythropoietin (EPO) by replacing the adhlacz gene with a 718 base pair PpuMI-NcoI fragment of human EPO cDNA (Wen et al. (1993) *Blood* 5:1507–1516) and by cloning a 2181 bp ClaI-EcoRI lacZ spacer fragment (noncoding) into the PmlI site of the vector. The cDNA sequence for human EPO is also depicted herein as FIG. 1 (SEQ ID. NO.:1).

C. Construction of pV4.1cmEpo.

A plasmid containing the murine erythropoietin (mEpo) coding region was constructed as follows. p4.1c is an expression vector that contains the CMV immediate-early promoter, a chimeric CMV-beta-globin intron, a polylinker, and the human growth hormone polyadenylation sequence. p4.1c was constructed using a synthetic DNA encoding the restriction sites NotI-MluI-Ecl136II-SstI-SfuI-SmaI-SfuI-ClaI-BglII-SnaBI-BstEII-PmlI-RsrII-NotI, and having the following nucleotide sequence: 5'-GCGGCC-GCACGCGTGAGCTCCGCGGTTCGAATC-CCGGGATTCGAACATCGATAAAAGATCTACGTAGGTAACCACGTGCGGACCGAGC-GGCCGC-3' (SEQ ID NO.:7), that was cloned into the blunted KasI and EarI(partial) sites of pUC119 to provide a 2757 bp intermediate plasmid. A 653 bp SpeI(blunted)-SacII (blunted) fragment encoding the CMV immediate early (CMV-IE) promoter, and a 488 bp SmaI-DraIII fragment containing the human growth hormone polyadenylation site, were cloned into the Ecl136II and SnaBI sites of the intermediate plasmid. A chimeric intron having the splice donor from the first intron of the CMV-IE gene, and the splice acceptor from the second intron of the human β-globin gene, was then inserted into the SmaI site of the plasmid in two steps. First, a DNA fragment encoding the CMV-IE gene first intron splice donor was produced by PCR using isolated CMV DNA (strain ad169) as template, and the following primers: GGCCGGGAACGGTGCATT (SEQ ID NO.:8) and GGGCAAGGGGGTGGGCCTATA (SEQ ID NO.:9). The resulting 87 bp fragment was ligated into the SmaI site of the intermediate plasmid. The resulting construct was cleaved with BstXI and SmaI, blunted with T4 DNA polymerase, and a 398 bp DraI-EcoRI(blunt) fragment encoding the human β-globin second intron splice acceptor was ligated into the construct. The p4.1c plasmid was completed by ligation of a synthetic polylinker encoding the restriction sites: ClaI-EcoRI-SmaI-BamHI-XbaI-SalI-PstI-HinDIII-XhoI-Eco47III-XhoI-BglII, having the following nucleotide sequence:
5'-ATCGATTGAATTCCCCGGGGATCCTCTAGAGTCG-ACCTGCAGAAGCTTGCTCTCGAGCAGCGCT-GCTCGAGAGATCT-3' (SEQ ID NO.:10), between the ClaI and BglII sites of the intermediate plasmid.

p4.1c was digested with SmaI, and a 2812 bp SmaI (partial)-NcoI(blunted) fragment encoding all of the exons of the mouse EPO gene (obtained from the 17.1 kB phage lambda genomic clone (McDonald et al. (1986) *Mol Cell. Biol.* 6:842–848)) was inserted therein to obtain the p4.1cmEPO expression cassette. The Kozak sequence around the initiator methionine was changed to the optimally translated sequence CCACCATG using oligonucleotide directed mutagenesis. The sequence of the mutagenic oligonucleotide was
5' AGCTAGGCGCCACCATGGGGGTGC-3' (SEQ ID NO.:11).

The polylinker and LacZ alpha fragment expression cassette of pUC119 was replaced by a single Sse8387I site by ligation of the following synthetic DNA fragment into the plasmid vector (after digestion with AflII and EheI): 5'-GGCGCCCCTGCAGGACATGT-3' (SEQ ID NO.:12). The resulting plasmid was cut with Sse8387I, and the 4772 bp Sse8387I from pW1909adhlacZ (that contains the ITR-bounded lacZ expression cassette) was ligated therein. The resulting plasmid was called intermediate 1.

p4.1cmEPO was digested with NotI, and the 4582 bp fragment encoding the mEPO cassette was isolated. One copy of a synthetic DNA fragment that encodes the D region of the AAV ITR was ligated to each end. The sequence of the synthetic fragment was as follows: 5'-CGGCCGCAGGAACCCCTAGTGATGGAGTTGG-3' (SEQ ID NO.:13). The resulting product was ligated into the 2831 bp plasmid vector MscI fragment of intermediate 1 to provide the pV4.1cmEPO construct.

Viruses and Cell Lines

Adenovirus type 2 (Ad2), available from the American Type Culture Collection, ATCC, Catalogue Number VR846, was used as helper virus to encapsidate vectors.

The human 293 cell line (Graham et al. (1977) *J. Gen. Virol.* 36:59–72, available from the ATCC under Accession no. CRL1573), which has adenovirus E1a and E1b genes stably integrated in its genome, was cultured in complete Dulbecco's modified Eagle's media (DMEM; Bio-Whittaker, Walkersville, Md.) containing 4.5 g/L glucose, 10% heat-inactivated fetal bovine serum (FBS; Hyclone, Logan, Utah), 2 mM glutamine, and 50 units/mL penicillin and 50 µg/mL streptomycin.

The C2C12 murine myoblast cell line, available from the ATCC, Catalogue Number CRL1772, was cultured in DMEM with 20% fetal calf serum (FCS), 1% chick embryo extract and 5 µg/mL gentamicin.

Fetal human skeletal myoblasts (Clonetics) were cultured in Hams F-12 human growth medium, containing 20% FCS and 5 µg/mL gentamicin.

The above cell lines were incubated at 37° C. in 5% $CO_2$, and were routinely tested and found free of mycoplasma contamination.

Production of Recombinant AAV Virions

Recombinant AAV virions were produced in human 293 cells as follows. Subconfluent 293 cells were cotransfected by standard calcium phosphate precipitation (Wigler et al. (1979) *Proc. Natl. Acad. Sci USA* 76:1373–1376) with one of the AAV vector/helper plasmid constructs pW1909adhLacZ or pW1909EPO; or with pV4.1cmEpo and the pW1909 helper construct. After 6 hours, the transfected cells were infected with Ad2 in fresh medium at a multiplicity of infection (MOI) of 2, and incubated at 37° C. in 5% $CO_2$ for 70 hours prior to harvest. Pelleted cells were lysed in Tris buffer (10 mM Tris, 150 mM NaCl, pH 8.0) by three cycles of freeze-thaw. The lysate was clarified of cell debris by centrifugation at 12,000×g, and the crude-cell lysate was layered onto a cesium chloride cushion for isopyknic gradient centrifugation. Recombinant AAV virions (rAAV-LacZ, rAAV-hEPO, or rAAV-mEPO virions) were extracted from the resulting gradient by isolating the fractions with an average density of approximately 1.38 g/mL, resuspended in Hepes buffered saline (HBS) containing 50 mM Hepes (pH 7.4) and 150 mM NaCl. The preparations were then heated at 56° C. for approximately 1 hour to inactivate Ad2.

Assay of rAAV by Dot-blot Hybridization

Recombinant AAV virions were DNase I digested, proteinase K treated, phenol-chloroform extracted, and DNA precipitated with sodium acetate-glycogen (final concentrations=0.3M sodium acetate and 160 µg/mL, respectively). DNA samples were denatured (200 µL of 2×alkaline solution (0.8M NaOH, 20 mM EDTA) added to DNA sample) for 10 minutes, then added to appropriate wells in a dot-blot apparatus, and blotted onto wet Zeta Probe membrane (BioRad), by applying suction until wells were empty. Then, 400 µL of 1×alkaline solution was added; after 5 minutes, wells were emptied by suction. The membrane was rinsed in 2×SSC (Sambrook et al., supra) for 1 min, drained, air dried on filter paper, then baked in vacuum at 80° C. for 30 min. The membrane was then prehybridized for 30 min at 65° C. with 10 mL hybridization buffer (7% SDS, 0.25M Sodium Phosphate, pH 7.2, 1 mM EDTA). Buffer was replaced with 10 mL fresh solution, freshly boiled probe added, and hybridized overnight at 65° C. The membrane was washed twice with 25 mL of wash-1 buffer (5% SDS, 40 mM sodium phosphate, pH 7.2, 1 mM EDTA) for 20 min at 65° C. and twice with wash-2 buffer (1% SDS, 40 mM sodium phosphate, pH 7.2, 1 mM EDTA). The membrane was wrapped in plastic film, exposed to radiographic film, and appropriate dots excised from the membrane to determine radioactivity by scintillation counting, and quantitated by comparison with standards. Titers of rAAV virion were routinely in the range of approximately $10^{13}$ genomes/mL.

Assay for Contaminating Helper Adenovirus

Contaminating infectious adenovirus was assayed as follows. Samples from the purified rAAV virion stocks were added to 50% confluent 293 cells (cultured in 12 well dishes at $1 \times 10^5$ cells/well), and the cultures were passaged for 30 days (e.g., the cultures were split 1 to 5, every 3 days) or until the culture exhibited 100% cytopathic effect (CPE) due to adenovirus infection. Cultures were examined daily for CPE, and the day upon which each experimental culture showed 100% CPE was noted. Reference 293 cell cultures infected with a range of known amounts of adenovirus type-2 (from 0 to $1 \times 10^7$ plaque forming units (pfu)/culture) were also prepared and treated in the same manner. A standard curve was then prepared from the data obtained from the reference cultures, where the adenovirus pfu number was plotted against the day of 100% CPE. The titer of infectious adenovirus type-2 in each experimental culture was then readily obtained as determined from the standard curve. The limit of detection of the assay was 100 pfu/mL. The presence of wild-type AAV contamination, analyzed by dot-blot hybridization, was approximately 7 logs lower than recombinant virion concentration.

Differentiation of Myoblasts

C2C12 myoblasts were transduced either while actively dividing, or as a differentiated cell culture. Differentiation was induced by placing subconfluent myoblasts in murine differentiation medium (DMEM containing 2% horse serum and standard concentrations of glutamine and penicillin-streptomycin) for an interval of five days prior to transduction in order to induce myoblast fusion and formation of differentiated myotubes.

Fetal human skeletal myoblasts were differentiated in human differentiation medium (DMEM containing 10% horse serum and 5 µg/mL gentamicin). Verification of differentiation was performed by microscopic analysis to determine the presence of multinucleated myotubes in culture.

EXAMPLE 1
In vitro Transduction of Murine Myotubes and Myoblasts

In order to determine if differentiated cultured muscle cells are appropriate targets for recombinant AAV virion transduction, and to assess the ability of such cells to express a transduced gene, the following study was carried out. Murine C2C12 cells were selected since these cells have been extensively studied as a model for mammalian myogenesis (Blau et al. (1993) *Trends Genet.* 9:269–274), and can be induced to differentiate by growth in reduced serum medium.

In the study, C2C12 myoblasts (dividing cells) were seeded in cell culture plates at a density of $2 \times 10^4$ cells/cm$^2$, maintained in growth media (GM) until confluent, split, and then either cultured in GM or cultured for 5 days in murine DM. Differentiation was verified by the microscopic presence of multinucleate myotubes, representing fused myoblasts (differentiated C2C12 cells).

The C2C12 myotubes and myoblasts were transduced in culture with purified rAAV-hEPO virions at a MOI of $10^5$ in OptiMEM (Gibco BRL). In the myotube cultures, DM was added after virion adsorption. The culture media of the transduced cells was changed 24 hours prior to collection of supernatants at 3, 8 and 14 days following transduction. Secretion of hEPO was assessed by ELISA using the human erythropoietin Quantikine IVD kit (available from R and D Systems, Minneapolis, Minn.) according to manufacturer's recommendations.

Figure 3:
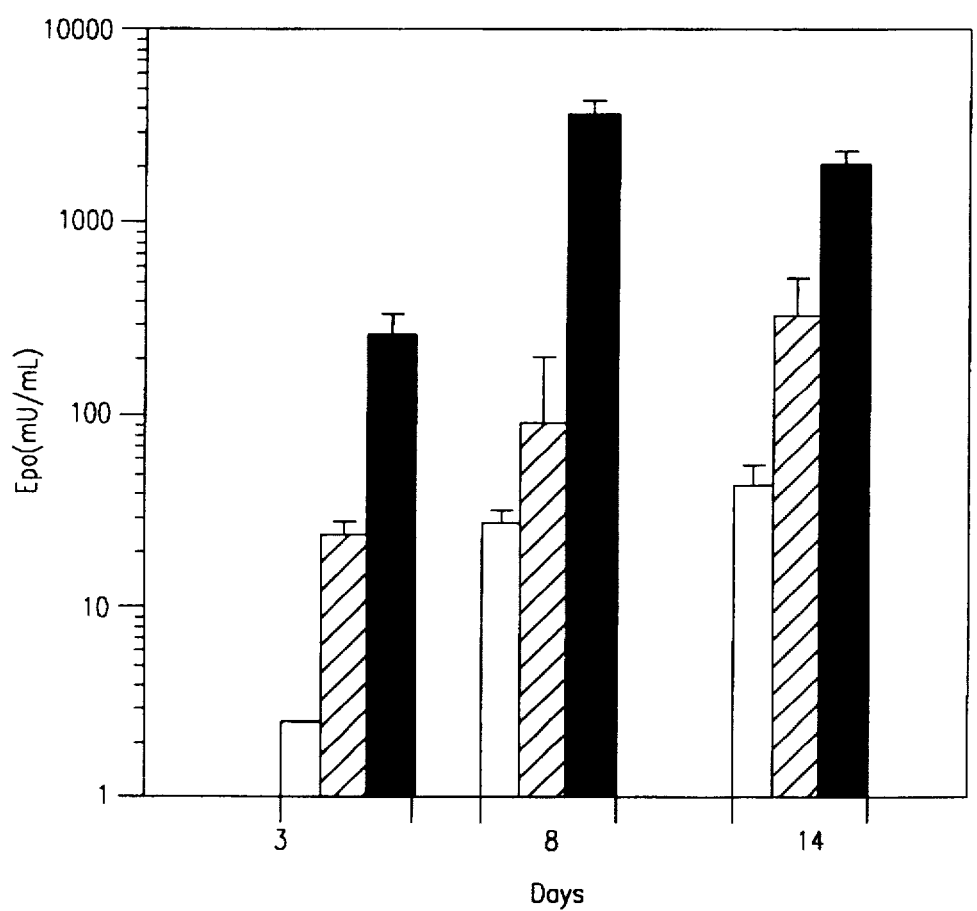
FIG. 3 shows the secretion of human erythropoietin (hEPO) by C2C12 myotubes transduced with rAAV-hEPO as described in Example 1. Confluent C2C12 myoblasts were differentiated into myotubes and transduced with $3 \times 10^8$ (open bar), $3 \times 10^9$ (cross-hatched bar), or $3 \times 10^{10}$ (solid bar) rAAV-hEPO. Secretion of EPO was measured 3, 8, and 14 days after transduction. Control rAAV-LacZ myotubes secreted <2.5 mU/mL EPO. The bar graph depicts mean production of EPO/well/24 hour as determined in triplicate cultures ±the standard error of mean (SEM).

The results of the study show that hEPO is secreted from both the transduced myotubes and myoblasts. The levels of hEPO secretion increased in the myotubes over the first seven days post-transduction (FIG. 2). As can be seen by reference to FIG. 3, a dose-dependent increase in the secretion of hEPO was also observed in the transduced C2C12 myotubes. Eight days post-transduction of the myotubes, hEPO levels peaked at >3400 mU/mL. These data demonstrate that transduction with rAAV-hEPO virions of both myotubes or myoblasts results in hEPO secretion by the transduced cells, and that in short-term myotube cultures, hEPO is synthesized and secreted in a dose-dependent manner.

EXAMPLE 2
In vitro Transduction of Human Myotubes Using rAAV-hEPO Virions To determine if differentiated primary human muscle cells are able to express hEPO following transduction with rAAV-hEPO virions, the following study was carried out. Primary fetal human skeletal myoblasts were seeded in cell culture plates at a density of $2 \times 10^4$ cells/cm$^2$, grown to confluence in appropriate growth media, and then cultured for 14 days in human DM. Differentiation was verified by microscopic examination for multinucleate cells. In vitro transduction was carried out by adding purified rAAV-hEPO virions to the cultured myotubes in OptiMEM medium (Gibco BRL). DM was added to the cultures after virion adsorption. Control cultures were rAAV-LacZ-transduced myotubes.

Culture media was changed 24 hours prior to collection of supernatants at day 3, 8 and 14 post transduction. Secreted EPO levels were assayed by ELISA as described above in Example 1.

Figure 4:
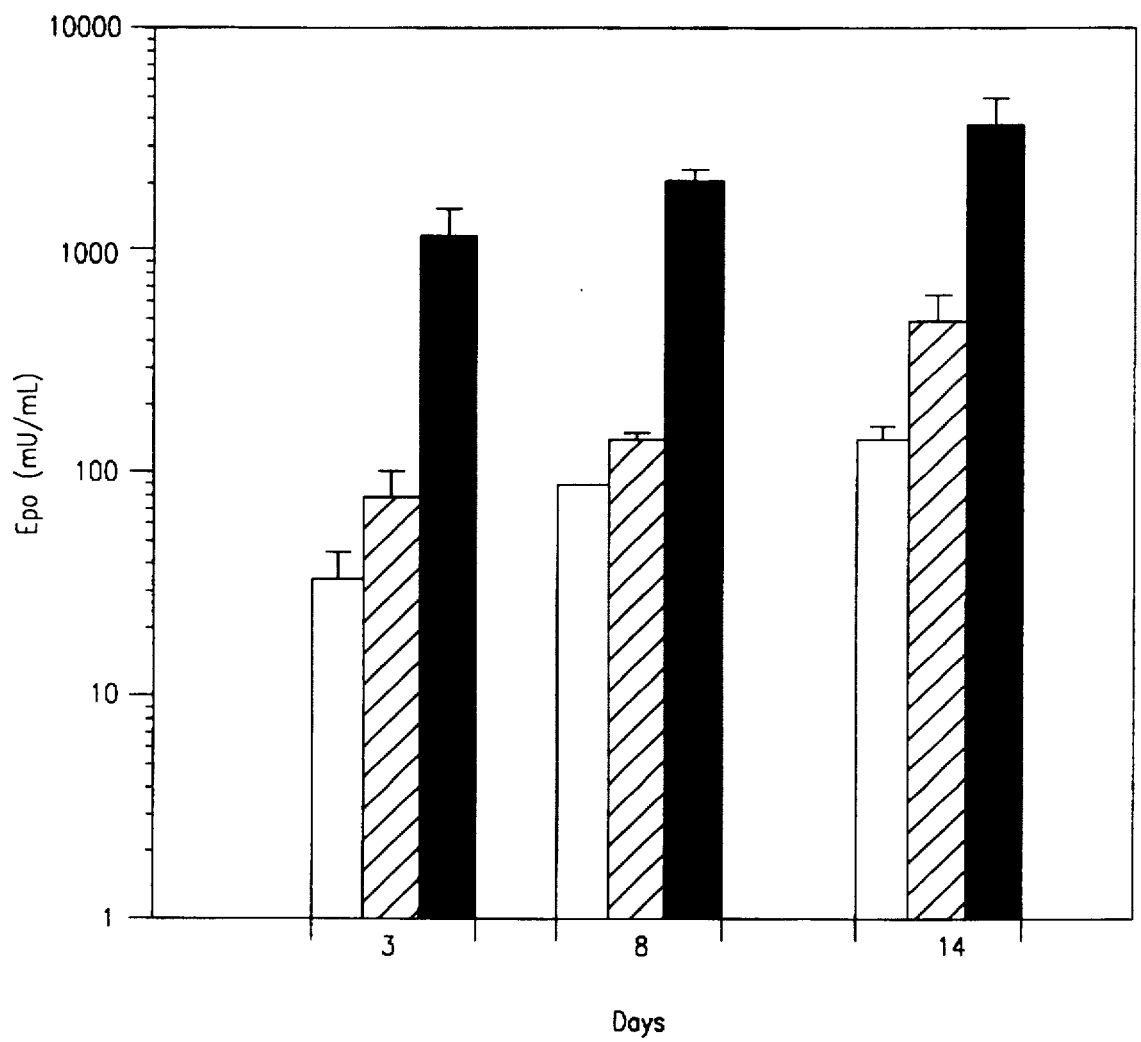
FIG. 4 shows the secretion of human erythropoietin (hEPO) by primary human myotubes transduced with rAAV-hEPO as described in Example 2. Confluent human myoblasts were differentiated into myotubes by culture for 14 days in reduced-serum media, then transduced with $3 \times 10^8$ (open bar), $3 \times 10^9$ (cross-hatched bar), or $3 \times 10^{10}$ (solid bar) rAAV-hEPO. Secretion of EPO was measured 3, 8 and 14 days after transduction. Control myotubes transduced with rAAV-LacZ secreted <2.5 mU/mL EPO. The bar graph depicts mean production of EPO/well/24 hour as determined in triplicate cultures ±SEM.

As can be seen in FIG. 4, the transduced human myotubes secreted hEPO into the culture in a dose-dependent manner. No detectable EPO activity was measured in the control cultures. Secretion of EPO increased over the 14-day interval post-transduction. These data demonstrate that primary human myotubes transduced by recombinant AAV virions are capable of expressing and secreting erythropoietin.

EXAMPLE 3
Systemic Delivery of Human Erythropoietin in vivo by Intramuscular Administration of rAAV-hEPO Recombinant AAV virions encoding hEPO were administered to adult healthy Balb/c mice in vivo to determine if a systemic level of hEPO can be produced, and a biological response obtained. At various time points after administration, blood was obtained from the orbital venous plexus under anesthesia. Serum hEPO levels were determined by ELISA as described above. Red cell counts were done by hemocytometer, hematocrit was determined by centrifugation of blood in micro-capillary tubes, and hemoglobin concentration was analyzed by cyanmethemoglobin assay (DMA, Arlington, Tex.) according to manufacturer's specifications and compared with a standard (Stanbio Laboratory, San Antonio, Tex.) analyzed at 570 nm on a spectrophotometer. Reticulocytes were analyzed by either new methylene blue stain, or by FACS analysis of thiazole orange stained peripheral blood samples (RETIC-COUNT®, Becton-Dickinson, Mountain View, Calif.); the results of data obtained by either of these methods were similar. Peripheral leukocyte count and differential were performed by modified Wright-Giemsa stain (Sigma Diagnostics, St. Louis, Mo.) according to the manufacturer's recommendations.

An initial experiment revealed that high levels of hEPO and elevated hematocrits were maintained for >100 days in mice injected IM with $6.5 \times 10^{11}$ rAAV-hEPO. Adult female Balb/c mice were injected IM in both hind limbs with a single administration of virions at dosages ranging from $3 \times 10^9$ to $3 \times 10^{11}$ rAAV-hEPO. Control animals were injected with rAAV-LacZ. The resulting serum hEPO levels were analyzed and are reported below in Table I. As can be seen, a well-defined dose-response was obtained 20, 41, 62 and 83 days post injection.

Figure 5:
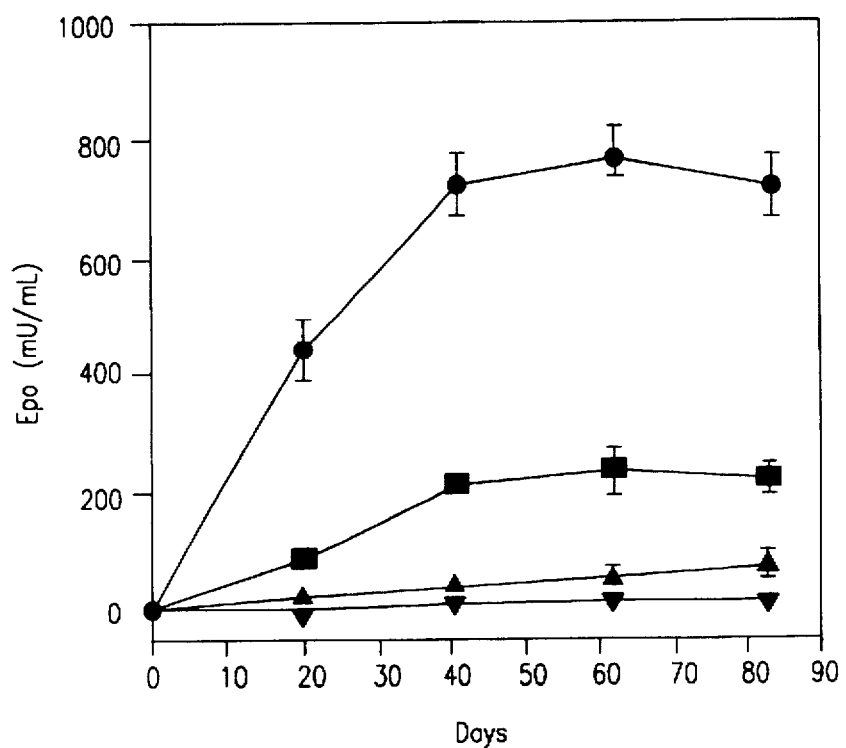
FIG. 5 depicts the time course of EPO secretion in Balb/c mice after IM injection with rAAV-hEPO. Adult Balb/c mice were injected IM with $1 \times 10^{10}$ (▼), $3 \times 10^{10}$ (▲), $1 \times 10^{11}$ (■), or $3 \times 10^{11}$ (●) rAAV-hEPO at day =0, and serum EPO levels measured at various time points post injection. Reported values represent means (n=4) ±SEM.

The time course of hEPO secretion by animals receiving rAAV-hEPO is depicted in FIG. 5. As can be seen, serum levels of hEPO increased with time to plateau at from 6 to 8 weeks after injection.

A comparison of the expression of hEPO by animals injected IM with rAAV-hEPO ($3 \times 10^{11}$ single-stranded genomes) and animals injected IM with the pW1909EPO plasmid ($1.4 \times 10^{13}$ double-stranded genomes in 100 µg DNA) shows that the recombinant virions gave rise to significantly greater levels of EPO expression. As reported in Table I, 20 days post-injection, recombinant virion-injected animals had serum levels of 445±98 mU/mL, while the plasmid-injected animals had levels of 8±10 mU/mL. At 41 days post-injection, the recombinant virion levels had risen to 725±112 mU/mL, while the plasmid levels had dropped below the level of detection. The animals receiving rAAV-hEPO exhibited approximately 60-fold more circulating hEPO with 100-fold less input genomes at 20 days post-injection, or approximately 6000-fold greater secretion per genome. At 41 days post-injection, this difference was even greater, since the plasmid expression was below the level of detection.

TABLE I

EPO Expression and Hematocrit: rAAV-hEPO Dose-Response

| | Days after Administration | | | | | | | |
|---|---|---|---|---|---|---|---|---|
| | 20 days | | 41 days | | 62 days | | 83 days | |
| Dose | EPO | HCT | EPO | HCT | EPO | HCT | EPO | HCT |
| $3 \times 10^{11}$ | 445 ± 98 | 74.2 ± 1.2 | 725 ± 112 | 82.3 ± 1.2 | 769 ± 61 | 86.5 ± 1.4 | 723 ± 253 | 88.5 ± 0.7 |
| $1 \times 10^{11}$ | 85 ± 14 | 72.8 ± 1.5 | 212 ± 23 | 79.5 ± 1.7 | 234 ± 75 | 83.2 ± 0.2 | 220 ± 51 | 83.2 ± 2 |
| $3 \times 10^{10}$ | 17 ± 5 | 60.0 ± 3.5 | 34 ± 17 | 74.7 ± 3.2 | 55 ± 28 | 78.7 ± 2.0 | 73 ± 45 | 80.0 ± 3 |
| $1 \times 10^{10}$ | 3 ± 1 | 52.9 ± 1.8 | 11 ± 3 | 61.5 ± 1.9 | 12 ± 8 | 68.4 ± 4.6 | 15 ± 5 | 70.8 ± 8 |
| $3 \times 10^{9}$ | <2.5 | 49.9 ± 1.4 | <2.5 | 53.5 ± 2.5 | <2.5 | 57.0 ± 2.4 | 4 ± 4 | 57.5 ± 3 |
| i.v. | 7 ± 3 | 54.7 ± 3.2 | 13 ± 2.0 | <64.4 ± 5.3 | 10.1 ± 0.7 | 70.8 ± 8 | 21 ± 10 | 74.6 ± 7 |
| Control | <2.5 | 48.9 ± 1.0 | <2.5 | 49.1 ± 0.8 | <2.5 | 48.1 ± 0.7 | <2.5 | 48.2 ± 9 |
| Plasmid | 8 ± 10 | 50 ± 3.0 | <2.5 | 50.2 ± 1.0 | <2.5 | 47.8 ± 0.9 | N.D; | N.D. |

Values representing means ± standard deviation (SD). EPO = serum levels of human EPO (mU/mL) in Balb/c mice; HCT = hematocrit (%); N.D. = not done; i.v. = intravenous injection with $3 \times 10^{11}$ rAAV-hEPO; Plasmid = injection with 100 μg plasmid DNA ($1.4 \times 10^{13}$ double-stranded plasmid molecules); Control = injection with $3 \times 10^{11}$ particles of rAAV-lacZ.

Figure 6:
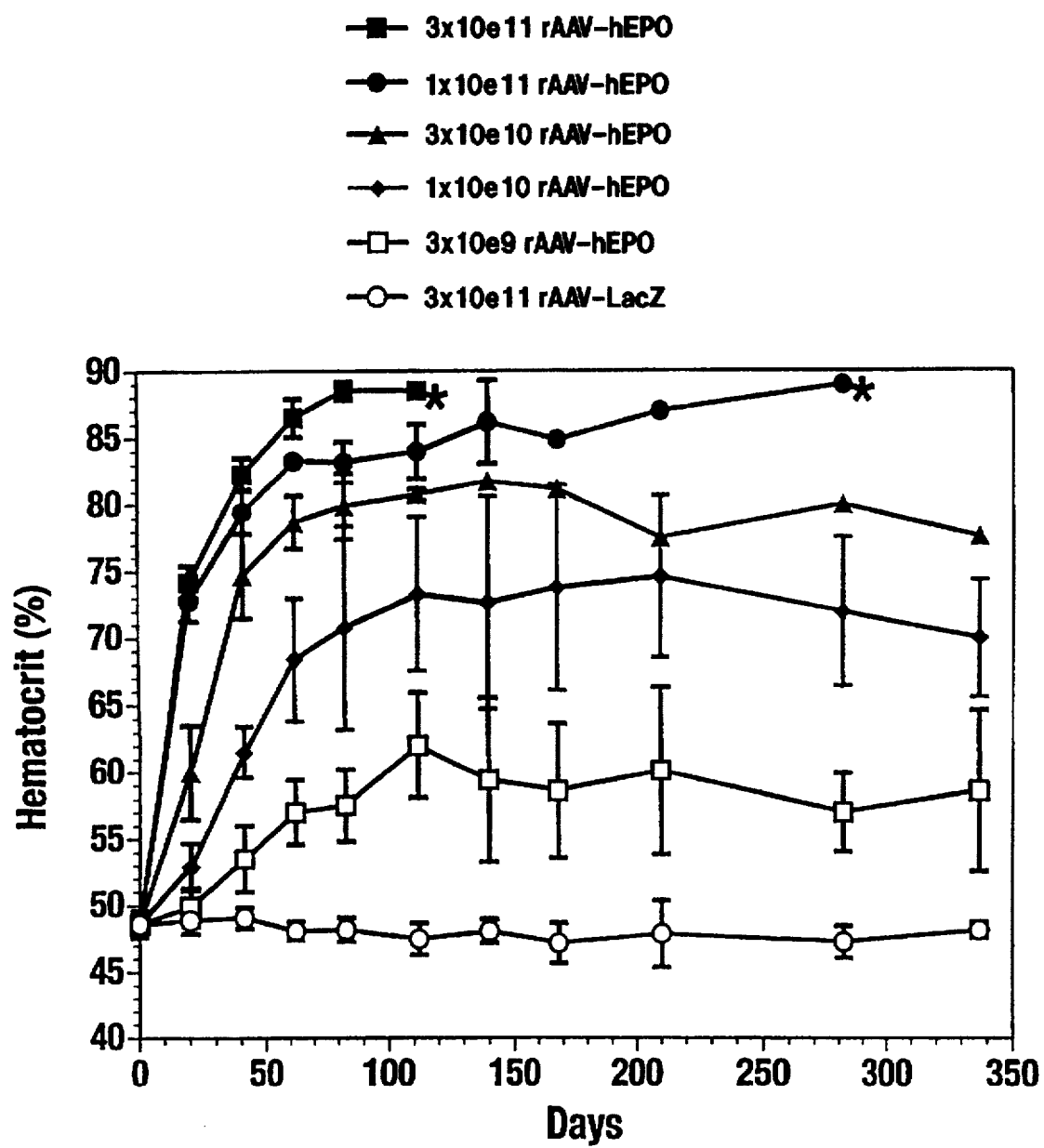
FIG. 6 depicts long-term hematocrit levels in animals treated with rAAV-hEPO. The reported values are means, and the error bars denote standard deviation. For the control group of animals (receiving rAAV-LacZ) n=3. For the rest of the values, n=4, except: n=3 for the group receiving $1 \times 10^{10}$ rAAV-hEPO at time points >day 112, and for the group receiving $1 \times 10^{11}$ at day 140; n=2 for the group receiving $3 \times 10^{11}$ rAAV-hEPO at time points >day 83; and n=1 for the group receiving $3 \times 10^{11}$ rAAV-hEPO at day 112, and for the group receiving $1 \times 10^{11}$ rAAV-hEPO at days 210 and 282. Asterisks indicate the last time point evaluated for groups in which all animals died.

The biological activity of secreted hEPO can be monitored by elevation of hematocrit in the experimental animals. A comparison of circulating hEPO levels versus hematocrit up to 83 days after administration is reported in Table I, above. The comparison shows that hematocrit increased with time and increasing recombinant virion dose in the treated animals. Long-term EPO expression and hematocrit levels were also monitored in a portion of the experimental animals. As reported in Table II below, serum levels of human EPO in treated animals remained constant over 282 days after administration of rAAV-hEPO. As depicted in FIG. 6, the long-term hematocrit levels also remained constant in the treated animals monitored up to 340 days after administration of rAAV-hEPO. Control animals had undetectable levels of hEPO (<2.5 mU/mL, the lower limit of detection for the assay).

These results indicate that persistent and stable high-level secretion of hEPO, with a corresponding elevation in hematocrit, is established following a single IM administration of rAAV-hEPO.

TABLE II

EPO EXPRESSION: rAAV-hEPO DOSE-RESPONSE

| | Days After Administration | | |
|---|---|---|---|
| Dose | 41 Days EPO | 140 Days EPO | 282 Days EPO |
| $1 \times 10^{11}$ | 212 ± 23[1] | 280 ± 62 | 283[3] |
| $3 \times 10^{10}$ | 34 ± 17[1] | 32 ± 12[2] | 29 ± 16[2] |
| $1 \times 10^{10}$ | 11 ± 3[1] | 14 ± 10 | 11 ± 8 |
| $3 \times 10^{9}$ | <2.5[1] | <2.5[1] | <2.5[1] |
| Control | <2.5 | <2.5 | <2.5 |

Values represent means ± S.D.; values are serum levels of human EPO in Balb/c mice in mU/mL. For all values, n = 3, except for following values: [1]n = 4; [2]n = 2, and values are averages; and [3]n = 1.

EXAMPLE 4
A Comparison of hEPO Secretion from rAAV-hEPO Administered by IM or IV Routes A comparison of the circulating levels of hEPO resulting from IM and IV routes of administration was analyzed to determine which method of gene delivery results in higher levels of systemic hEPO. Balb/c mice were injected with $3 \times 10^{11}$ rAAV-hEPO using either the IM route as described above, or intravenously (IV) in PBS in a total volume of 50 μL via the lateral tail vein. Serum hEPO levels were determined by ELISA using the methods described above.

As shown in Table I, hEPO levels resulting from the IV administrations were significantly lower than the group that received the virions by the IM route. In particular, at 20 days post-injection, the IM route resulted in levels of hEPO of 445±98 mU/mL, while the IV route produced 7±3.0 mU/mL. At 41 days post-injection, the EPO level observed with the IM route was 725±112 as compared with 13±2.0 mU/mL by IV, or approximately 60-fold more efficacious. These data demonstrate that the IM route of injection resulted in higher systemic levels of hEPO, and suggest that interstitial delivery in muscle results in improved transduction by the recombinant AAV virions.

EXAMPLE 5
Treatment of Thalassemia using Recombinant AAV Virions in Thalassemic Animal Models In order to determine whether IM administration of rAAV-mEPO virions in thalassemic mice would result in phenotypic improvement of anemia, the following study was carried out. Two murine models were selected for experimentation, one strain having a naturally occurring genetic defect in beta globin and which displays clinical features analogous to human beta-thalassemia intermedia, and a more severely affected transgenic thalassemic strain.

A. Mouse strains and animal procedures.

6 to 8 week old female C57BL6 mice were obtained from Simonsen (Gilroy, Calif.). Mice with beta-thalassemia intermedia (strain T/T), having a C57BL6 parental background and harboring a naturally occurring mutation in beta-globin (Johnson et al. (1981) Proc. Natl. Acad. Sci. USA 78:3138; Goldberg et al. (1986) J. Biol. Chem. 261:12368), were obtained from Dr. E. Rubin, Lawrence Berkeley laboratory, University of California, Berkeley, Calif. The T/T strain displays clinical features analogous to beta-thalassemia intermedia. Skow et al. (1983) Cell 34:1043; Popp et al. (1985) Ann. NY Acad. Sci. 445:432. Transgenic thalassemic mice (strain T/N), derived from a C57BL6 parental background (Paszty, C. (in press), "Mouse Models for the α- and β-Thalassemias: The Power of Transgenic and Gene Knock-Out Approaches," Intl. J. Ped. Hematol.), were also provided by Dr. Rubin.

Bleeding of animals was by tail vein collection. The recombinant AAV virions were administered by percutaneous injection such that approximately 35 μL of virions diluted in pyrogen-free saline was delivered to each of two sites in each hindlimb (for a total of 140 μL per animal).

B. Assessment of hematologic parameters.

Peripheral blood samples were collected from the tail vein into tubes containing heparin. Peripheral blood smears were air-dried and stained by modified Wright-Giemsa (Sigma, St. Louis, Mo.) prior to analysis. Collected blood was diluted in PBS and red cells were counted in a hemocytometer. Quantitation of blood hemoglobin was performed by diluting blood in cyanmethemoglobin (DMA, Arlington, Tex.) at a 1:250 ratio, and measuring absorbance of 200 μL aliquots of the resulting solution at 570 nm in an ELISA reader. Absorbance was compared against a commercially available standard (Stanbio, San Antonio, Tex.).

Hematocrit was analyzed by centrifugation of blood in microcapillary tubes. Reticulocyte count was determined by thiazole orange staining (Becton-Dickinson, Mountain View, Calif.), followed by fluorescence activated cell sorting (FACS) analysis (FACSTAR®, Becton-Dickinson). Total serum iron and red cell membrane "deformability" were analyzed using known methods. Clark et al. (1983) *Blood* 61:889–910.

Weights of spleens and hearts were determined at the time of necropsy. Histopathological analyses of thin sections of formalin-fixed bone marrow and spleen were also performed.

C. Baseline hematologic characteristics of T/T and T/N mice.

The hematologic profile of T/T mice has been previously described. Skow et al. (1983) *Cell* 34:1043; Popp et al. (1985) *Ann. NY Acad. Sci.* 445:432. Review of Wright-Giemsa stained smears of peripheral blood from T/T mice revealed marked poikilocytosis, anisocytosis and hypochromia. Baseline measurements of red blood cell counts, hemoglobin and hematocrit revealed moderate anemia. Marked peripheral reticulocytosis has been described in these mice (Skow, et al. and Popp et al., supra) and was confirmed in the analysis reported below in Table III. T/N mice are more severely affected, and show more marked anemia and reticulocytosis, as well as greater heart and spleen weights at autopsy. Paszty, C. (in press), "Mouse Models for the α- and β-Thalassemias: The Power of Transgenic and Gene Knock-Out Approaches," *Intl. J. Ped. Hematol.*

TABLE III

Effect on Hematologic Parameters of Intramuscular Administration of rAAV-hEPO in T/T Thalassemic Mice

| Animals: | $T_0$ | | | | $T_1$ | | | |
|---|---|---|---|---|---|---|---|---|
| Virion | Hg | Hct | Rbc | Rtc | Hg | Hct | Rbc | Rtc |
| T/T: rAAV-hEPO | 11.5 | 32.8 | 5.0 | 16.7 | 19.2 | 61.2 | 8.3 | 18.5 |
| T/T: rAAV-lacZ | 11.0 | 32.6 | 5.2 | 19.0 | 9.0 | 29.6 | 4.5 | 21.9 |
| C57: rAAV-hEPO | 16.5 | 45.2 | 6.6 | 3.5 | 25.5 | 80.9 | 13.1 | 6.0 |
| C57: rAAV-lacZ | 16.5 | 45.2 | 6.6 | 3.5 | 13.8 | 46.3 | 6.6 | 3.2 |

$T_0$ = Baseline blood values; $T_1$ = values 8 weeks post-injection. Hg = hemoglobin (g/dL); Hct = hematocrit (%); Rbc = red blood cell count ($\times 10^6$/mL); Rtc = reticulocytes (%). Values are means; T/T:rAAV-hEPO (n = 10); for the other animal groups (n = 3). Standard deviations (s.d.) were <±10% of the mean values, except s.d. for $T_1$ Hct of T/T:rAAV-hEPO = 10.7.

D. Effects on anemia after IM injection of rAAV-mEPO in T/T mice.

Figure 7:
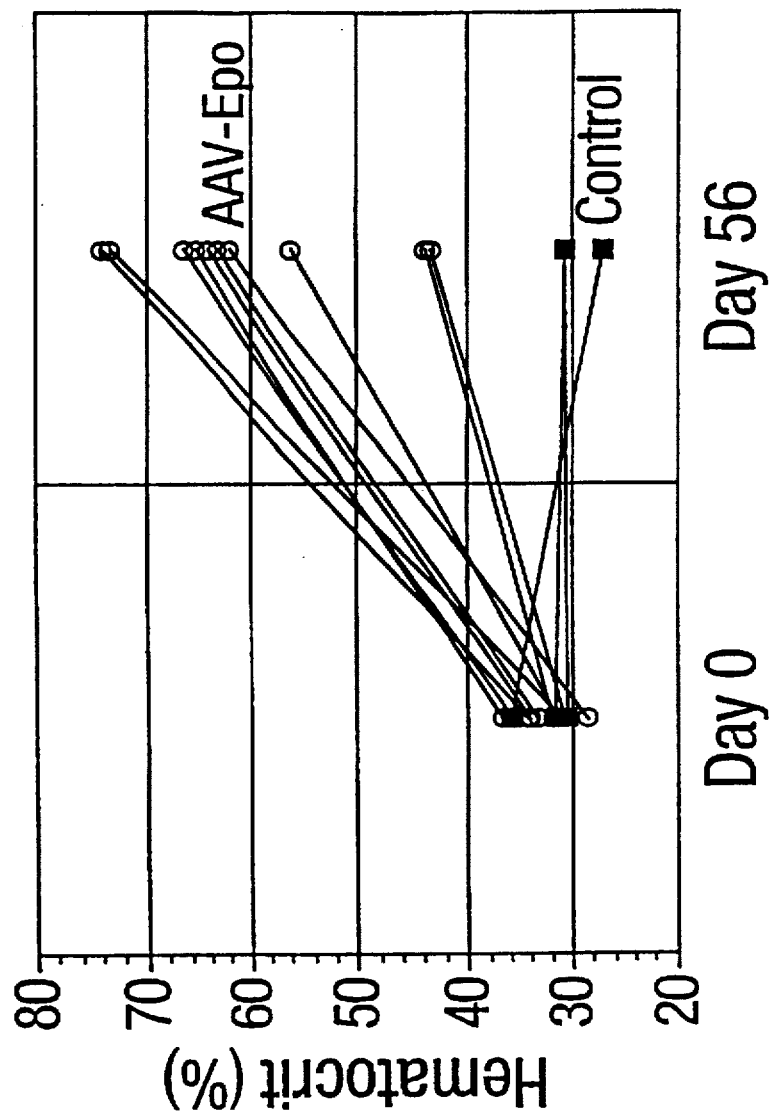
FIG. 7 shows mean hematocrit levels in T/T mice treated with a single IM administration of rAAV-mEPO virions as described in Example 5, Part D.

On day 27 after a single administration of rAAV-mEPO by IM injection, 10/10 of the treated T/T animals responded with an increase in the circulating red cell number, hemoglobin, hematocrit, and reticulocyte count (Table III). As can be seen, hematocrit levels rose approximately 1.6 fold above baseline. On day 58 post administration, hematologic parameters continued to increase, with mean hematocrits reaching approximately 1.9 fold higher than baseline values (FIG. 7, Table III).

Comparable increases in hematocrit (approximately 1.8 fold higher than baseline value) were also observed in normal C57BL6 mice that had received the IM rAAV-mEPO virions. Initial examination of reticulocyte counts 27 days after injection in the treated thalassemic animals demonstrated an increase over their baseline parameters, and over control animals (rAAV-LacZ-treated thalassemics). Control rAAV-LacZ virion-injected T/T thalassemic animals, and unaffected C57BL6 animals displayed no significant change in hematopoietic parameters.

E. Effects on anemia after IM injection of rAAV-mEPO virions in T/N mice.

Seven weeks after single administration of rAAV-mEPO by IM injection, 3/3 of the treated T/N animals responded with an increase in the circulating red cell number, hemoglobin, hematocrit, and reticulocyte count (Table IV). As can be seen by the results reported below in Table IV, all hematologic parameters in the treated T/N animals were increased relative to control animals (injected with rAAV-LacZ virions), which did not show any significant change.

TABLE IV

Effect on Hematologic Parameters of Intramuscular Administration of rAAV-hEPO in T/N Thalassemic Mice

| Animals: | $T_0$ | | | $T_1$ | | |
|---|---|---|---|---|---|---|
| Virion | Hg | Hct | Rbc | Hg | Hct | Rbc |
| T/N: rAAV-hEPO | 9.5 | 28.1 | 4.7 | 13.7 | 35.1 | 6.2 |
| T/N: rAAV-lacZ | 8.4 | 25.9 | 4.4 | 7.2 | 25.0 | 4.8 |

$T_0$ = Baseline values; $T_1$ = 7 weeks after vector injections. Hg = hemoglobin (g/dL); Hct = hematocrit (%); Rbc = red blood cell count ($\times 10^6$/μL). Values are mean values for T/N/epo (n = 3) with standard deviation of 12% of the mean values; for T/N/lacZ, values are the means, n = 2.

F. Effects on red cell deformability.

Figure 8:
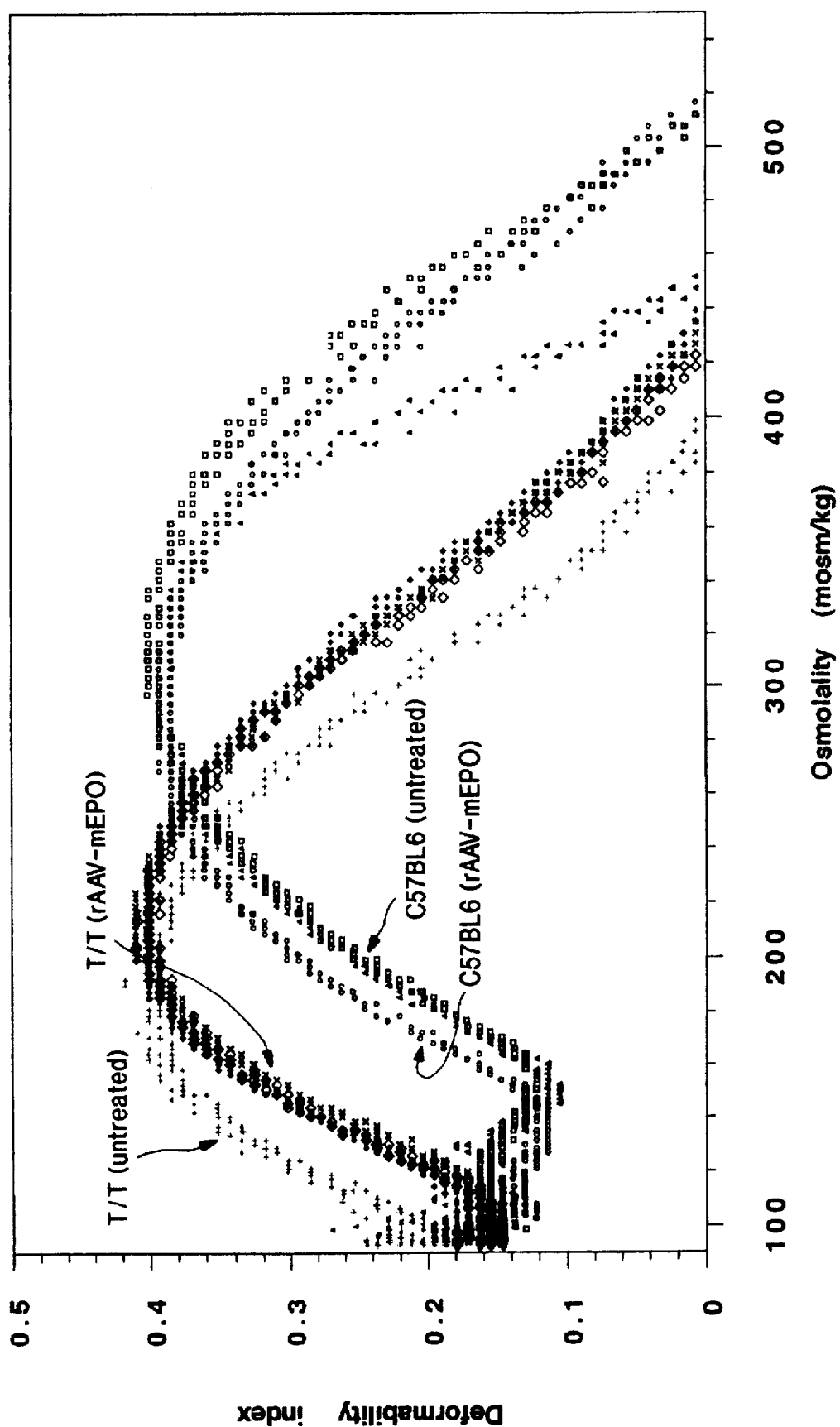
FIG. 8 shows red cell membrane deformability index in T/T mice treated with a single IM administration of rAAV-mEPO virions as described in Example 5, Part F.

To establish whether red blood cells in T/T animals treated with the rAAV-mEPO virions are functionally different than cells in nontreated T/T animals, analyses of red cell deformability were carried out using previously described methods. Clark et al., supra. As reported in Table V, below, and seen in FIG. 8, the results obtained from 4/10 of the treated T/T animals reveal that deformability of the red cell membrane was shifted more toward normal when compared to the control group. This suggests that the membrane shape of red blood cells in the treated T/T animals was more stable to changes in osmotic pressure relative to the red blood cells of untreated T/T animals.

TABLE V

Red Blood Cell Volume in T/T Mice Administered rAAV-hEPO

|  | Group 1 T/T (ctl) volume | Group 2 T/T + EPO volume | Group 3 C57 (ctl) volume | Group 4 C57 + EPO volume |
|---|---|---|---|---|
| 1 | 40.5 | 43.8 | 59.9 | 56.7 |
| 2 | 32.6 | 41.7 |  | 53.2 |
| 3 | 33.1 | 41.5 |  | 45.9 |
| 4 |  | 43.7 |  |  |
| 5 |  | 39.8 |  |  |
| 6 |  | 40.1 |  |  |
| 7 |  | 42.2 |  |  |
| Average | 35.4 | 41.8 | 59.9 | 51.9 |
| SD | 4.4 | 1.6 |  | 5.5 |

These data demonstrate that a single IM administration of rAAV-mEPO virions results in sustained improvement of anemia in beta-thalassemic (T/T) mice in 10/10 animals tested. Plateau values of hematocrit, red blood cells, hemoglobin, and reticulocytes were reached approximately 8 weeks after administration of the recombinant virion preparation. Increases in these hematologic parameters occurred in parallel throughout the experimental group. Initially, reticulocyte counts increased up to 4 weeks post injection. However, subsequent analysis at 8 weeks post injection showed a decline in reticulocyte percentages, which returned to baseline (pre-injection) levels. The persistent increases in hematocrit that were observed suggest that red cell survival was prolonged due to administration of the rAAV-mEPO virions. The data obtained in the osmotically induced deformability studies also suggests that the red cell membranes were more stable in treated T/T mice as compared with the untreated T/T animals.

The results observed in the more severely affected T/N animals also indicate that IM rAAV-mEPO virion therapy is successful in increasing red cell parameters. Thus, EPO secretion in treated thalassemic animals was sufficient to improve therapeutic parameters of anemia, whether intermediate or severe in nature.

Accordingly, novel methods for transferring EPO genes into cells, both in vitro and in vivo, have been described. Further, methods for treating thalassemia in thalassemic animals have also been described. Although preferred embodiments of the subject invention have been described in some detail, it is understood that obvious variations can be made without departing from the spirit and the scope of the invention as defined by the appended claims.

Deposits of Strains Useful in Practicing the Invention

A deposit of biologically pure cultures of the following strain was made with the American Type Culture Collection, 12301 Parklawn Drive, Rockville, Md., under the provisions of the Budapest Treaty. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

This deposit is provided merely as a convenience to those of skill in the art, and is not an admission that a deposit is required. A license may be required to make, use, or sell the deposited materials, and no such license is hereby granted.

| Strain | Deposit Date | ATCC No. |
|---|---|---|
| pGN1909 | July 20, 1995 | 69871 |

---

We claim:

1. A composition, comprising:
(a) recombinant AAV virions which comprise an AAV vector containing a nucleic acid molecule encoding erythropoietin operably linked to control elements that direct the transcription and translation thereof; and
(b) a pharmaceutically acceptable excipient.

2. A method of treating anemia in a mammalian subject, said method comprising administering to muscle of said subject a therapeutically effective amount of the pharmaceutical composition of claim 1 such that said recombinant AAV virions transduce muscle cells in said subject, and said nucleic acid molecule is expressed by said transduced cells at a level sufficient to increase a hematocrit of said subject.

3. The method of claim 2, wherein the anemia is an anemic disorder selected from the group consisting of anemia associated with chronic renal failure, cancer, cancer chemotherapy and antiviral therapy.

4. A method of treating a hemoglobinopathy in a mammalian subject, said method comprising administering to muscle of said subject a therapeutically effective amount of the pharmaceutical composition of claim 1 such that said recombinant AAV virions transduce muscle cells in said subject, and said nucleic acid molecule is expressed by said transduced cells at a level sufficient to increase a hematocrit of said subject.

5. The method of claim 4, wherein the hemoglobinopathy is selected from the group consisting of sickle cell disease and thalassemia.

6. The method of claim 2, wherein the muscle cells are derived from skeletal muscle.

7. The method of claim 6, wherein the muscle cells are skeletal myoblasts.

8. The method of claim 6, wherein the muscle cells are skeletal myocytes.

9. The method of claim 2, wherein the pharmaceutical composition is administered by intramuscular injection.

10. The method of claim 9, wherein the pharmaceutical composition is administered in a single dose.

11. The method of claim 9, wherein the pharmaceutical composition is administered in multiple doses.

12. The method of claim 2, wherein the nucleic acid molecule encodes native human erythropoietin.

13. The method of claim 2, wherein the nucleic acid molecule encodes native feline erythropoietin.

14. The method of claim 2, wherein the control elements comprise a muscle-specific promoter sequence.

15. The method of claim 2, wherein the control elements comprise an inducible promoter sequence.

16. The method of claim 2, wherein the pharmaceutical composition is administered to the subject in combination with an adjunctive pharmacological therapy.

17. The method of claim 16, wherein the adjunctive pharmacological therapy comprises administering a therapeutically effective amount of an agent selected from the group consisting of hydroxyurea, butyrate, clotrimazole, and combinations thereof.

18. A method of treating anemia in a mammalian subject, said method comprising:
  (a) introducing recombinant AAV virions into muscle cells in vitro to produce transduced muscle cells, wherein said recombinant AAV virions comprise an AAV vector having a nucleic acid molecule encoding erythropoietin operably linked to control elements that direct the transcription and translation thereof when present in muscle of said subject; and
  (b) administering directly into muscle of said subject a therapeutically effective amount of a composition comprising the transduced muscle cells from step (a) to deliver said transduced cells to muscle of said subject, whereafter said nucleic acid molecule is expressed by said transduced cells at a level sufficient to increase a hematocrit of said subject.

19. The method of claim 18, wherein the anemia is an anemic disorder selected from the group consisting of anemia associated with chronic renal failure, cancer, cancer chemotherapy and antiviral therapy.

20. The method of claim 18, wherein the anemia is a hemoglobinopathy.

21. The method of claim 20, wherein the hemoglobinopathy is selected from the group consisting of sickle cell disease and thalassemia.

22. The method of claim 18, wherein the muscle cells are derived from skeletal muscle.

23. The method of claim 22, wherein the muscle cells are skeletal myoblasts.

24. The method of claim 22, wherein the muscle cells are skeletal myocytes.

25. The method of claim 18, wherein the nucleic acid molecule encodes native human erythropoietin.

26. The method of claim 18, wherein the nucleic acid molecule encodes native feline erythropoietin.

27. The method of claim 18, wherein the control elements comprise a muscle-specific promoter sequence.

28. The method of claim 18, wherein the control elements comprise an inducible promoter sequence.

29. A method for delivering erythropoietin systemically to a mammalian subject, said method comprising administering directly into muscle of said subject the pharmaceutical composition of claim 1 such that said recombinant AAV virions transduce muscle cells in said subject and said nucleic acid molecule is expressed by said transduced cells to produce a systemic level of erythropoietin, thereby providing for an increased hematocrit of said subject.

30. The method of claim 29, wherein the nucleic acid molecule encodes native human erythropoietin.

31. The method of claim 29, wherein the nucleic acid molecule encodes native feline erythropoietin.

32. A method for delivering erythropoietin systemically to a mammalian subject, said method comprising:
  (a) introducing recombinant AAV virions into muscle cells in vitro to produce transduced muscle cells, wherein said recombinant AAV virions comprise an AAV vector having a nucleic acid molecule encoding erythropoietin operably linked to control elements that direct the transcription and translation thereof when present in muscle of said subject; and
  (b) administering directly into muscle of said subject a therapeutically effective amount of a composition comprising the transduced muscle cells from step (a) to deliver said transduced cells to muscle of said subject, whereafter said nucleic acid molecule is expressed by said transduced cells to produce a systemic level of erythropoietin, thereby providing for an increased hematocrit of said subject.

33. The method of claim 32, wherein the nucleic acid molecule encodes native human erythropoietin.

34. The method of claim 32, wherein the nucleic acid molecule encodes native feline erythropoietin.

* * * * *

UNITED STATES PATENT AND TRADEMARK OFFICE
Certificate

Patent No. 5,846,528                                                Patented: December 8, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gregory M. Podsakoff, Fullerton, CA (US); Gary J. Kurtzman; Menlo Park, CA (US); Barry J. Byrne, Baltimore, MD (US); Paul D. Kessler, Baltimore, MD (US).

Signed and Sealed this Fourth Day of March 2008.

PETER PARAS
*Supervisory Patent Examiner*
Art Unit 1632